(12) United States Patent
Wogulis et al.

(10) Patent No.: US 10,738,293 B2
(45) Date of Patent: Aug. 11, 2020

(54) CELLOBIOHYDROLASE VARIANTS AND POLYNUCLEOTIDES ENCODING SAME

(71) Applicant: Novozymes A/S, Bagsvaerd (DK)

(72) Inventors: Mark Wogulis, Davis, CA (US); Leslie Demars, Roseville, CA (US); Aubrey Jones, Davis, CA (US); Hanshu Ding, Davis, CA (US); David Osborn, Sacramento, CA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/081,168

(22) PCT Filed: Mar. 2, 2017

(86) PCT No.: PCT/US2017/020502
§ 371 (c)(1),
(2) Date: Aug. 30, 2018

(87) PCT Pub. No.: WO2017/151957
PCT Pub. Date: Sep. 8, 2017

(65) Prior Publication Data
US 2019/0085309 A1 Mar. 21, 2019

Related U.S. Application Data

(60) Provisional application No. 62/322,827, filed on Apr. 15, 2016, provisional application No. 62/302,219, filed on Mar. 2, 2016.

(51) Int. Cl.
*C12N 9/42* (2006.01)
*C12P 19/14* (2006.01)
(Continued)

(52) U.S. Cl.
CPC ............ *C12N 9/2437* (2013.01); *C07K 14/42* (2013.01); *C12N 15/52* (2013.01); *C12N 15/8241* (2013.01); *C12P 19/14* (2013.01); *C12Y 302/01004* (2013.01); *C12N 2015/8518* (2013.01)

(58) Field of Classification Search
None
See application file for complete search history.

(56) References Cited

U.S. PATENT DOCUMENTS 7,375,197 B2   5/2008   Adney et al.
2014/0065671 A1*  3/2014  Stringer ......... C12Y 302/01091
                                            435/69.1
(Continued)

FOREIGN PATENT DOCUMENTS

WO   2004016760 A2   2/2004
WO   2005001065 A2   1/2005
(Continued)

OTHER PUBLICATIONS

UniProt Accession No. Q2GMP2_CHAGB, published Mar. 21, 2006 (Year: 2006).*

*Primary Examiner* — Richard C Ekstrom
(74) *Attorney, Agent, or Firm* — Kelly Reynolds

(57) ABSTRACT

The present invention relates to cellobiohydrolase variants, polynucleotides encoding the variants; nucleic acid constructs, vectors, and host cells comprising the polynucleotides; and methods of producing and using the variants.

17 Claims, 2 Drawing Sheets

Specification includes a Sequence Listing.

(51) Int. Cl.
*C12N 15/85* (2006.01)
*C07K 14/42* (2006.01)
*C12N 15/52* (2006.01)
*C12N 15/82* (2006.01)

(56) References Cited

U.S. PATENT DOCUMENTS

2015/0004655 A1* 1/2015 Wogulis ................ C12P 19/14
 435/99
2017/0152498 A1* 6/2017 Persillon ................ C12P 19/02

FOREIGN PATENT DOCUMENTS

| WO | 2005028636 A2 | 3/2005 |
| WO | 2011050037 A1 | 4/2011 |
| WO | 2011123450 A1 | 10/2011 |
| WO | 2012103288 A1 | 8/2012 |
| WO | 2013096603 A2 | 6/2013 |
| WO | 2013166312 A1 | 11/2013 |
| WO | 2015042543 A2 | 3/2015 |

* cited by examiner

```
            *         20         *         40         *         60
1 : ---------QQTMWGQCGGQGWTGPTICVAGATCSTQNPWYAQCTPAPTAPTTLQTTTTTS :  52
2 : VPL-EERQACSSVWGQCGGQNWSGPTCCASGSTCVYSNDYYSQCLPGAASSSSTRAASTT :  60
3 : APLVEERQACAAQWAQCGGFSWNGATCCQSGSYCSKINDYYSQCIPGEGPATSKSST---- :  57
4 : APVIEERQNCGAVWTQCGGNWQGPTCCASGSTCVAQNEWYSQCLPNSQVTSSTTPSSTST :  61
5 : -------QNCQTVWGQCGGQGWTGATSCVAGATCSTLNPYYAQCLPATATTTTTTTPTTT :  54
6 : -------QNCQTVWGQCGGQGWTGATSCVAGAACSTLNPYYAQCLPATATTTTTTTTTTT :  54
7 : -------QACQTVWGQCGGQGWTGATSCVAGAACSTLNPYYAQCLPATATTTTTTTTTTT :  54
8 : ---------QQTVWGQCGGQGWSGPTSCVAGAACSTLNPYYAQCIPGATATSTTLT----- :  47
9 : -------QAQQTVWGQCGGQGWSGPTSCVAGSTCSTQNPYYAQCIPGSTATSTTTSTTTT :  54

*         80         *        100         *        120
1 : ---SKSSTTTS-------SKSSTTTGGSGGGTTTSTSATITAAPSGNPYSGYQLYVNQEYS : 103
2 : ---SRVSPTTS-------RSSSATPPPGSTTTRVPPVGSGTATYSGNPFVGVTPWANAYYA : 111
3 : ---LPASTTTT-------QPTSTSTAGTSSTTKPPPAGSGTATYSGNPYSGVNLWANSYYR : 108
4 : SQRSTSTSSSTTRSGSSSSSSTTPPPVSSPVTSIPGGATSTASYSGNPFSGVRLFANDYYR : 122
5 : TSSTTTTSTTT-------TSTTTTPTTTTTTTSAPSGPTTTATASG-PFSGYQLYANPYYS : 107
6 : TSSTTTTSTTT-------SSTTTTPTTTTTTTTAPSSVTTTATASG-PFSGYQLYANPYYS : 107
7 : TSSTTTTSTTT-------SSTTTTPTTTTTTTSAPSGVTTTATASG-PFSGYQLYANPYYS : 107
8 : ---TTTAATTT-------SQTTTKPTTTGPTTSAP-----TVTASGNPFSGYQLYANPYYS :  93
9 : ---TTTSTTTT-------TTTTTTPPTTGPTTTAPPAATTTASASGNPFSGYQLYANPYYA : 105

*        140         *        160         *        180
1 : SEVYASAIPSLT-GTLVAKASAAAEVPSFLWLDTASKVPL-MGTYLQDIQAKNAAGANPPY : 162
2 : SEVSSLAIPSLT-GAMATAAAAVAKVPSFMWLDTLDKTPL-MEQTLADIRTANKNGGN--Y : 168
3 : SEVTNLAIPKLS-GAMATAAAKVADVPSYQWMDSFDHISL-MEDTLVDIRKANLAGGN--Y : 165
4 : SEVHNLAIPSMT-GTLAAKASAVAEVPSFQWLDRNVTIDTLMVQTLSQVRALNKAGANPPY : 182
5 : SEVHTLAIPSLTDGSLAPKASAVAKVPSFVWLDTAAKVPT-MGTYLADIQAKNKAGANPPI : 167
6 : SEVHTLAIPSLTDGSLAPKASAVAKVPSFVWLDTAAKVPT-MGTYLADIRAKNAAGANPPI : 167
7 : SEVHTLAIPSLTDGSLAPKATAVAKVPSFVWLDTAAKVPT-MGTYLADIRAQNAAGANPPI : 167
8 : SEVHTLAMPSLP-SSLQPKASAVAEVPSFVWLDVAAKVPT-MGTYLADIQAKNAGANPPI : 152
9 : SEVHSLAIPSLTDSSLAPKASAVAKVPSFVWLDTAAKVPT-MGTYLADIQAKNKAGANPPI : 165

*        200         *        220         *        240
1 : AGQFVVYDLPDRDCAALASNGEYSIANNGVANYKAYIDSIRALLVQYSNVHVILVIEPDSL : 223
2 : AGQFVVYDLPDRDCAALASNGEYSIADGGVAKYKNYIDTIRQIVVEYSDIRTLLVIEPDSL : 229
3 : AGQFVVYDLPDRDCAAAASNGEYSLDNDGANKYKNYIQTIKKIIQSYSDIRILLVIEPDSL : 226
4 : AAQLVVYDLPDRDCAAAASNGEFSIANGGAANYRSYIDAIRKHIIEYSDIRIILVIEPDSM : 243
5 : AGIFVVYDLPDRDCAALASNGEYSIANNGVANYKAYIDSIRAQLKKYSDVHTILVIEPDSL : 228
6 : AGIFVVYDLPDRDCAALASNGEYSIANNGVANYKAYIDSIRAQLVKYSDVHTILVIEPDSL : 228
7 : AGIFVVYDLPDRDCAALASNGEYSIANNGVANYKAYIDSIRAQLVKYSDVHTILVIEPDSL : 228
8 : AGIFVVYDLPDRDCAALASNGEYSIANNGVANYKAYIDAIRAQLVKYSDVHTILVIEPDSL : 213
9 : AGIFVVYDLPDRDCAALASNGEYSIANNGVANYKAYIDSIRAQLVKYSDVHTILVIEPDSL : 226
```

Fig. 1A

```
            *         260         *         280         *         300
1 : ANLVTNLNVQKCANAQSAYLECINYALTQLNLKNVAMYIDAGHAGWLGWPANLSPAAQLFA : 284
2 : ANLVTNLGTPKCANAQSAYLECINYAVTQLNLPNVAMYLDAGHAGWLGWPANQDPAAQLFA : 290
3 : ANLVTNMDVAKCAKAHDAYISLTNYAVTELNLPNVAMYLDAGHAGWLGWPANQGPAAKLFA : 287
4 : ANMVTNMNVAKCSNAASTYHELTVYALKQLNLPNVAMYLDAGHAGWLGWPANIQPAAELFA : 304
5 : ANLVTNLNVAKCANAQSAYLECVNYALTQLNLPNVAMYLDAGHAGWLGWPANLGPAAQLFA : 289
6 : ANLVTNLNVAKCANAQSAYLECINYALTQLNLPNVAMYLDAGHAGWLGWPANLSPAAQLFA : 289
7 : ANLVTNLNVAKCANAQSAYLECINYALTQLNLPNVAMYLDAGHAGWLGWPANLSPAAQLFA : 289
8 : ANLVTNLNVAKCANAQSAYLECVDYALKQLNLPNVAMYLDAGHAGWLGWPANLGPAATLFA : 274
9 : ANLVTNLNVAKCANAQSAYLECVDYALKQLNLPNVAMYLDAGHAGWLGWPANLGPAAQLFA : 287

*         320         *         340         *         360
1 : SVYQNASSPAAVRGLATNVANYNAWSIATCPSYTQGDPNCDEQKYINALAPLLQQQGWSSV : 345
2 : NVYKNASSPRALRGLATNVANYNGWNITSPPSYTQGNAVYNEKLYIHAIGPLLANHGWSNA : 351
3 : SIYKDAGKPAALRGLATNVANYNAWSLSSAPPYTQGASIYDEKSFIHAMGPLLEQNGWPGA : 348
4 : GIYNDAGKPAAVRGLATNVANYNAWSIASAPSYTSPNPNYDEKHYIEAFSPLLNSAGFP-A : 364
5 : SVYKNAGSPAAVRGLATNVANYNAWSISSCPSYTQGDSNCDEKRYINALAPLLKAQGFSDA : 350
6 : SVYKNAGSPAALRGLATNVANYNAWSISTCPSYTQGDSNCDEKRYINALAPLLKAQGFPDA : 350
7 : SVYKNAGSPAALRGLATNVANYNAWSISTCPSYTQGDSNCDEKRYINALAPLLKEQGFSDA : 350
8 : KVYTDAGSPAAVRGLATNVANYNAWSLSTCPSYTQGDPNCDEKKYINAMAPLLKEAGF-DA : 334
9 : KVYKNAGSPAAVRGLATNVANYNAWSISTCPSYTQGDPNCDEKRYINALAPLLKENGFPDA : 348

*         380         *         400         *         420
1 : HFITDTGRNGVQPTKQNAWGDWCNVIGTGFGVRPTTNTGDPLEDAFVWVKPGGESDGTSNS : 406
2 : FFITDQGRSGKQPTGQQQWGDWCNVIGTGFGIRPSANTGDSLLDSFVWVKPGGECDGTSDS : 412
3 : HFITDQGRSGKQPTGQIQWGDWCNSKGTGFGIRPSANTGDSLLDAFVWVKPGGESDGTSDT : 409
4 : RFIVDTGRNGKQPTGQQQWGDWCNVKGTGFGVRPTANTGHELVDAFVWVKPGGESDGTSDT : 425
5 : HFIMDTSRNGVQPTKQQAWGDWCNVIGTGFGVRPTTNTGDPLEDAFVWVKPGGESDGTSDT : 411
6 : HFIMDTSRNGVQPTKQQAWGDWCNVIGTGFGVRPTTNTGDPLQDAFVWVKPGGESDGTSDT : 411
7 : HFIMDTSRNGVQPTKQQAWGDWCNVIGTGFGVRPTTNTGDALQDAFVWVKPGGESDGTSDT : 411
8 : HFIMDTSRNGVQPTKQNAWGDWCNVIGTGFGVRPSTNTGDPLQDAFVWIKPGGESDGTSNS : 395
9 : HFIMDTSRNGVQPTKQQAWGDWCNVIGTGFGVRPTTNTGDPLQDAFVWVKPGGESDGTSNT : 409

*         440         *         460
1 : TSPRYDAHCGYSDALQPAPEAGTWFEAYFEQLLTNANPSF- : 446
2 : SAPRFDSHCALPDALQPAPQAGAWFQAYFVQLLTNANPSFL : 453
3 : SATRYDYHCGASAALQPAPEAGTWFQAYFEQLLTNANPSFL : 450
4 : SAARYDHCGLSDALQPAPEAGQWFQAYFEQLLTNANPPF- : 465
5 : SAARYDAHCGYSDALQPAPEAGTWFQAYFEQLLTNANPSF- : 451
6 : SAARYDAHCGYSDALQPAPEAGTWFQAYFEQLLTNANPSF- : 451
7 : SAARYDAHCGYSDALQPAPEAGTWFQAYFEQLLTNANPSF- : 451
8 : TSPRYDAHCGYSDALQPAPEAGTWFQAYFEQLLTNANPSF- : 435
9 : SSPRYDAHCGYSDALQPAPEAGTWFQAYFEQLLTNANPSF- : 449
```

Fig. 1B

CELLOBIOHYDROLASE VARIANTS AND POLYNUCLEOTIDES ENCODING SAME

CROSS-REFERENCE TO RELATED APPLICATIONS

This application is a 35 U.S.C. § 371 national application of PCT/US2017/020502 filed Mar. 2, 2017, which claims priority or the benefit under 35 U.S.C. § 119 of U.S. Provisional Application No. 62/322,827 filed Apr. 15, 2016 and U.S. Provisional Application No. 62/302,219 filed Mar. 2, 2016, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to cellobiohydrolase variants, polynucleotides encoding the variants, methods of producing the variants, and methods of using the variants.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars can easily be fermented by yeast into ethanol.

WO 2004/016760 discloses variants of *Hypocrea jecorina* Cel7A cellobiohydrolase I.

WO 2005/001065 discloses variants of *Humicola grisea* Cel7A cellobiohydrolase I, *Hypocrea jecorina* cellobiohydrolase I, and *Scytalidium thermophilium* cellobiohydrolase I.

WO 2005/028636 discloses variants of *Hypocrea jecorina* Cel7A cellobiohydrolase I.

WO 2011/050037 discloses *Aspergillus fumigatus* cellobiohydrolase variants with improved thermostability.

WO 2011/050037 discloses *Thielavia terrestris* cellobiohydrolase variants with improved thermostability.

WO 2011/123450 discloses *Aspergillus fumigatus* cellobiohydrolase variants with improved thermostability.

WO 2012/103288 discloses *Talaromyces leycettanus* cellobiohydrolase variants with improved thermostability.

WO 2013/096603 discloses *Talaromyces byssochlamydoides* cellobiohydrolase variants with improved thermostability.

U.S. Pat. No. 7,375,197 discloses *Trichoderma reesei* cellobiohydrolase I variants.

The present invention provides cellobiohydrolase variants with improved properties compared to its parent.

SUMMARY OF THE INVENTION

The present invention relates to cellobiohydrolase variants, comprising a substitution at one or more (e.g., several) positions corresponding to positions 201, 243, 286, and 343 of the polypeptide of SEQ ID NO: 1, wherein the cellobiohydrolase variants have cellobiohydrolase activity.

The present invention also relates to cellobiohydrolase variants, comprising a variant catalytic domain, wherein the variant catalytic domain comprises a substitution at one or more (e.g., several) positions corresponding to positions 201, 243, 286, and 343 of SEQ ID NO: 1, wherein the cellobiohydrolase variants have cellobiohydrolase activity.

The present invention also relates to isolated polynucleotides encoding the variants; nucleic acid constructs, vectors, and host cells comprising the polynucleotides; and methods of producing the variants.

The present invention also relates to processes for degrading a cellulosic material, comprising: treating the cellulosic material with an enzyme composition comprising a cellobiohydrolase variant of the present invention. In one aspect, the processes further comprise recovering the degraded cellulosic material.

The present invention also relates to processes of producing a fermentation product, comprising: (a) saccharifying a cellulosic material with an enzyme composition comprising a cellobiohydrolase variant of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition comprising a cellobiohydrolase variant of the present invention. In one aspect, the fermenting of the cellulosic material produces a fermentation product. In another aspect, the processes further comprise recovering the fermentation product from the fermentation.

BRIEF DESCRIPTION OF THE FIGURES

FIGS. 1A and 1B show an alignment of a *Talaromyces leycettanus* cellobiohydrolase (SEQ ID NO: 1), a *Trichoderma reesei* cellobiohydrolase (SEQ ID NO: 2), a *Fusarium solani* cellobiohydrolase (SEQ ID NO: 3), a *Myceliophthora thermophila* cellobiohydrolase (SEQ ID NO: 4), a cellobiohydrolase (SEQ ID NO: 5), a cellobiohydrolase (SEQ ID NO: 6), a cellobiohydrolase (SEQ ID NO: 7), an *Aspergillus fumigatus* cellobiohydrolase (SEQ ID NO: 8), and a cellobiohydrolase (SEQ ID NO: 9).

DEFINITIONS

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. Acetylxylan esterase activity can be determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. Alpha-L-arabinofuranosidase activity can be determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. Alpha-glucuronidase activity can be determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Auxiliary Activity 9 polypeptide: The term "Auxiliary Activity 9 polypeptide" or "AA9 polypeptide" means a polypeptide classified as a lytic polysaccharide monooxygenase (Quinlan et al., 2011, *Proc. Natl. Acad. Sci. USA* 108: 15079-15084; Phillips et al., 2011, *ACS Chem. Biol.* 6: 1399-1406; Li et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic material by an enzyme having cellulolytic activity. Cellulolytic enhancing activity can be determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40° C.-80° C., e.g., 40° C., 45° C., 50° C., 55° C., 60° C., 65° C., 70° C., 75° C., or 80° C. and a suitable pH, such as 4-9, e.g., 4.5, 5.0, 5.5, 6.0, 6.5, 7.0, 7.5, 8.0, 8.5, or 9.0, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST™ 1.5 L (Novozymes A/S, Bagsærd, Denmark) and beta-glucosidase as the source of the cellulolytic activity, wherein the beta-glucosidase is present at a weight of at least 2-5% protein of the cellulase protein loading. In one aspect, the beta-glucosidase is an *Aspergillus oryzae* beta-glucosidase (e.g., recombinantly produced in *Aspergillus oryzae* according to WO 02/095014). In another aspect, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The AA9 polypeptide can be used in the presence of a soluble activating divalent metal cation according to WO 2008/151043 or WO 2012/122518, e.g., manganese or copper.

The AA9 polypeptide can also be used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01%

TWEEN® 20 at pH 5, 40° C. One unit of beta-xylosidase is defined as 1.0 µmole of p-nitrophenolate anion produced per minute at 40° C., pH 5 from 1 mM p-nitrophenyl-beta-D-xyloside in 100 mM sodium citrate containing 0.01% TWEEN® 20.

Carbohydrate binding module: The term "carbohydrate binding module" means a domain within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose. In an embodiment, the carbohydrate binding module has the sequence of amino acids 19-54 of SEQ ID NO: 1. In another embodiment, the carbohydrate binding module has the sequence of amino acids 25-65 of SEQ ID NO: 2. In another embodiment, the carbohydrate binding module has the sequence of amino acids 25-63 of SEQ ID NO: 3. In another embodiment, the carbohydrate binding module has the sequence of amino acids 26-62 of SEQ ID NO: 4. In another embodiment, the carbohydrate binding module has the sequence of amino acids 4-39 of SEQ ID NO: 5. In another embodiment, the carbohydrate binding module has the sequence of amino acids 4-39 of SEQ ID NO: 6. In another embodiment, the carbohydrate binding module has the sequence of amino acids 2-39 of SEQ ID NO: 7. In another embodiment, the carbohydrate binding module has the sequence of amino acids 20-57 of SEQ ID NO: 8. In another embodiment, the carbohydrate binding module has the sequence of amino acids 2-40 of SEQ ID NO: 9.

Catalase: The term "catalase" means a hydrogen-peroxide:hydrogen-peroxide oxidoreductase (E.C. 1.11.1.6 or E.C. 1.11.1.21) that catalyzes the conversion of two hydrogen peroxides to oxygen and two waters.

Catalase activity can be determined by monitoring the degradation of hydrogen peroxide at 240 nm based on the following reaction:

$$2H_2O_2 \rightarrow 2H_2O + O_2$$

The reaction is conducted in 50 mM phosphate pH 7 at 25° C. with 10.3 mM substrate ($H_2O_2$). Absorbance is monitored spectrophotometrically within 16-24 seconds, which should correspond to an absorbance reduction from 0.45 to 0.4. One catalase activity unit can be expressed as one pmole of $H_2O_2$ degraded per minute at pH 7.0 and 25° C.

Catalytic domain: The term "catalytic domain" means the region of an enzyme containing the catalytic machinery of the enzyme. In an embodiment, the catalytic domain has the sequence of amino acids 107-464 of SEQ ID NO: 1. In another embodiment, the catalytic domain has the sequence of amino acids 107-471 of SEQ ID NO: 2. In another embodiment, the catalytic domain has the sequence of amino acids 108-468 of SEQ ID NO: 3. In another embodiment, the catalytic domain has the sequence of amino acids 119-482 of SEQ ID NO: 4. In another embodiment, the catalytic domain has the sequence of amino acids 94-451 of SEQ ID NO: 5. In another embodiment, the catalytic domain has the sequence of amino acids 94-451 of SEQ ID NO: 6. In another embodiment, the catalytic domain has the sequence of amino acids 94-451 of SEQ ID NO: 7. In another embodiment, the catalytic domain has the sequence of amino acids 97-454 of SEQ ID NO: 8. In another embodiment, the catalytic domain has the sequence of amino acids 90-449 of SEQ ID NO: 9.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman N°1 filter paper, microcrystalline cellulose, bacterial cellulose, algal cellulose, cotton, pretreated lignocellulose, etc. The most common total cellulolytic activity assay is the filter paper assay using Whatman N°1 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 25° C.-80° C., e.g., 25° C., 30° C., 35° C., 40° C., 45° C., 50° C., 55° C., 60° C., 65° C., 70° C., 75° C., or 80° C., and a suitable pH, such as 3-9, e.g., 3.0, 3.5, 4.0, 4.5, 5.0, 5.5, 6.0, 6.5, 7.0, 7.5, 8.0, 8.5, or 9.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in *Handbook on Bioethanol* (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicellulose, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is arundo, bagasse, bamboo, corn cob, corn fiber, corn stover, miscanthus, rice straw, sugar cane straw, switchgrass, or wheat straw.

In another embodiment, the cellulosic material is aspen, eucalyptus, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Dissolved Oxygen Saturation Level: The saturation level of oxygen is determined at the standard partial pressure (0.21 atmosphere) of oxygen. The saturation level at the standard partial pressure of oxygen is dependent on the temperature and solute concentrations. In an embodiment where the temperature during hydrolysis or saccharification is 50° C., the saturation level would typically be in the range of 5-5.5 mg oxygen per kg slurry, depending on the solute concentrations. Hence, a concentration of dissolved oxygen of 0.5 to 10% of the saturation level at 50° C. corresponds to an amount of dissolved oxygen in a range from 0.025 ppm (0.5×5/100) to 0.55 ppm (10×5.5/100), such as, e.g., 0.05 to 0.165 ppm, and a concentration of dissolved oxygen of 10-70% of the saturation level at 50° C. corresponds to an amount of dissolved oxygen in a range from 0.50 ppm (10×5/100) to 3.85 ppm (70×5.5/100), such as, e.g., 1 to 2 ppm. In an embodiment, oxygen is added in an amount in the range of 0.5 to 5 ppm, such as 0.5 to 4.5 ppm, 0.5 to 4 ppm, 0.5 to 3.5 ppm, 0.5 to 3 ppm, 0.5 to 2.5 ppm, or 0.5 to 2 ppm. In one aspect, the dissolved oxygen concentration during saccharification is in the range of 0.5-10% of the saturation level, such as 0.5-7%, such as 0.5-5%, such as 0.5-4%, such as 0.5-3%, such as 0.5-2%, such as 1-5%, such as 1-4%, such as 1-3%, such as 1-2%.

Endoglucanase: The term "endoglucanase" means a 4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. Feruloyl esterase activity can be determined using 0.5 mM p-nitrophenylferulate as substrate in 50 mM sodium acetate pH 5.0.

One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide; wherein the fragment has cellobiohydrolase activity. In one aspect, a fragment contains at least 380 amino acid residues, at least 400 amino acid residues, or at least 420 amino acid residues. In another aspect, a fragment contains at least 85% of the amino acid residues, e.g., at least 90% of the amino acid residues or at least 95% of the amino acid residues of the parent cellobiohydrolase.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, Current Opinion In Microbiology 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, Pure & Appl. Chem. 59: 1739-1752, at a suitable temperature such as 40° C.-80° C., e.g., 40° C., 45° C., 50° C., 55° C., 60° C., 65° C., 70° C., 75° C., or 80° C., and a suitable pH such as 4-9, e.g., 4.0, 4.5, 5.0, 5.5, 6.0, 6.5, 7.0, 7.5, 8.0, 8.5, or 9.0.

Hemicellulosic material: The term "hemicellulosic material" means any material comprising hemicelluloses. Hemicelluloses include xylan, glucuronoxylan, arabinoxylan, glucomannan, and xyloglucan. These polysaccharides contain many different sugar monomers. Sugar monomers in hemicellulose can include xylose, mannose, galactose, rhamnose, and arabinose. Hemicelluloses contain most of the D-pentose sugars. Xylose is in most cases the sugar monomer present in the largest amount, although in softwoods mannose can be the most abundant sugar. Xylan contains a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, Adv. Polym. Sci. 186: 1-67. Hemicellulosic material is also known herein as "xylan-containing material".

Sources for hemicellulosic material are essentially the same as those for cellulosic material described herein.

In the processes of the present invention, any material containing hemicellulose may be used. In a preferred aspect, the hemicellulosic material is lignocellulose.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, glucose tolerance, catalytic efficiency, catalytic rate, chemical stability, oxidation stability, pH activity, pH stability, specific activity, stability under storage conditions, substrate binding, substrate cleavage, substrate specificity, substrate stability, surface properties, thermal activity, and thermostability. In particular, the improved property is glucose tolerance, catalytic efficiency, and catalytic rate.

Improved catalytic efficiency: The term "improved catalytic efficiency" means that the ratio of the maximum number of catalytic cycles per unit time an enzyme can carry out under given conditions, such as temperature, pH, dissolved molecules and solute type, divided by the concentration of substrate required to reach one half of that maximum number of catalytic cycles is greater for the variant compared to the parent of the variant.

Improved catalytic rate: The term "improved catalytic rate" means a cellobiohydrolase variant converting more substrate to product in a given period of time compared to the same given amount of the parent of the variant in the same period of time under the same conditions, such as temperature, substrate concentration, substrate composition, pH, salt concentration, inhibitor concentration.

Improved glucose tolerance: The term "improved glucose tolerance" means a cellobiohydrolase variant having an improved catalytic rate when mixed with inhibiting concentrations of glucose compared to the catalytic rate of the parent of the variant in the presence of the same concentration of glucose and under the same reaction conditions.

Isolated:

The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Laccase: The term "laccase" means a benzenediol:oxygen oxidoreductase (E.C. 1.10.3.2) that catalyzes the following reaction: 1,2- or 1,4-benzenediol+$O_2$=1,2- or 1,4-benzosemiquinone+$2H_2O$.

Laccase activity can be determined by the oxidation of syringaldazine (4,4'-[azinobis(methanylylidene)]bis(2,6-dimethoxyphenol)) to the corresponding quinone 4,4'-[azobis (methanylylidene])bis(2,6-dimethoxycyclohexa-2,5-dien-1-one) by laccase. The reaction (shown below) is detected by an increase in absorbance at 530 nm.

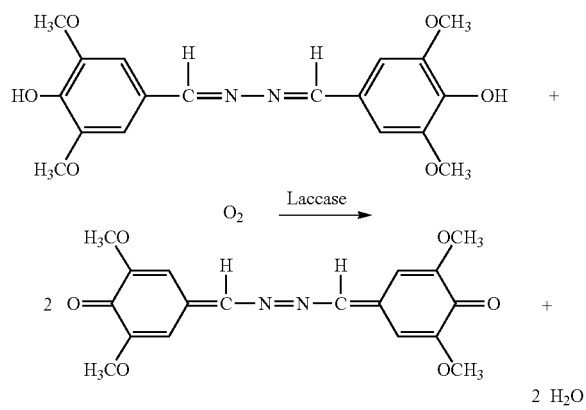

The reaction is conducted in 23 mM MES pH 5.5 at 30° C. with 19 µM substrate (syringaldazine) and 1 g/L polyethylene glycol (PEG) 6000. The sample is placed in a spectrophotometer and the change in absorbance is measured at 530 nm every 15 seconds up to 90 seconds. One laccase unit is the amount of enzyme that catalyzes the conversion of 1 µmole syringaldazine per minute under the specified analytical conditions.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having cellobiohydrolase activity.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent cellobiohydrolase: The term "parent" or "parent cellobiohydrolase" means a cellobiohydrolase to which an alteration, i.e., a substitution, insertion, and/or deletion, at one or more (e.g., several) positions, is made to produce the enzyme variants of the present invention. The parent may be a naturally occurring (wild-type) polypeptide or a variant or fragment thereof.

Peroxidase: The term "peroxidase" means an enzyme that converts a peroxide, e.g., hydrogen peroxide, to a less oxidative species, e.g., water. It is understood herein that a peroxidase encompasses a peroxide-decomposing enzyme. The term "peroxide-decomposing enzyme" is defined herein as a donor:peroxide oxidoreductase (E.C. number 1.11.1.x, wherein x=1-3, 5, 7-19, or 21) that catalyzes the reaction reduced substrate $(2e^-)$+ROOR'→oxidized substrate+ROH+R'OH; such as horseradish peroxidase that catalyzes the reaction phenol+$H_2O_2$→quinone+$H_2O$, and catalase that catalyzes the reaction $H_2O_2$+$H_2O_2$→$O_2$+$2H_2O$. In addition to hydrogen peroxide, other peroxides may also be decomposed by these enzymes.

Peroxidase activity can be determined by measuring the oxidation of 2,2'-azino-bis(3-ethylbenzthiazoline-6-sulfonic acid (ABTS) by a peroxidase in the presence of hydrogen peroxide as shown below. The reaction product $ABTS_{ox}$ forms a blue-green color which can be quantified at 418 nm.

The reaction is conducted in 0.1 M phosphate pH 7 at 30° C. with 1.67 mM substrate (ABTS), 1.5 g/L TRITON® X-405, 0.88 mM hydrogen peroxide, and approximately 0.040 units enzyme per ml. The sample is placed in a spectrophotometer and the change in absorbance is measured at 418 nm from 15 seconds up to 60 seconds. One peroxidase unit can be expressed as the amount of enzyme required to catalyze the conversion of 1 µmole of hydrogen peroxide per minute under the specified analytical conditions.

Pretreated cellulosic or hemicellulosic material: The term "pretreated cellulosic or hemicellulosic material" means a cellulosic or hemicellulosic material derived from biomass by treatment with heat and dilute sulfuric acid, alkaline pretreatment, neutral pretreatment, or any pretreatment known in the art.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are a gap open penalty of 10, a gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having cellobiohydrolase activity.

Variant: The term "variant" means a polypeptide having cellobiohydrolase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the cellobiohydrolase activity of the polypeptide of SEQ ID NO: 1.

Wild-type cellobiohydrolase: The term "wild-type" cellobiohydrolase means a cellobiohydrolase produced by a naturally occurring microorganism, such as a bacterium, yeast, or filamentous fungus found in nature.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrmann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Xylan degrading activity can be determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem.* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

Conventions for Designation of Variants

For purposes of the present invention, the cellobiohydrolase of SEQ ID NO: 1 is used to determine the corresponding amino acid residue in another cellobiohydrolase. The amino acid sequence of another cellobiohydrolase is aligned with the cellobiohydrolase of SEQ ID NO: 1, and based on the alignment, the amino acid position number corresponding to any amino acid residue in the polypeptide of SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix.

Identification of the corresponding amino acid residue in another cellobiohydrolase can be determined by alignment of multiple polypeptide sequences using several computer programs including, but not limited to MUSCLE (multiple sequence comparison by log-expectation; version 3.5 or later; Edgar, 2004, *Nucleic Acids Research* 32: 1792-1797); MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When another cellobiohydrolase has diverged from the cellobiohydrolase of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example, the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly, the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to isolated cellobiohydrolase variants, comprising a substitution at one or more (e.g., several) positions corresponding to positions 201, 243, 286, and 343 of the polypeptide of SEQ ID NO: 1, wherein the variant has cellobiohydrolase activity.

Variants

The present invention provides cellobiohydrolase variants, comprising a substitution at one or more (e.g., several) positions corresponding to positions 201, 243, 286, and 343 of SEQ ID NO: 1, wherein the variant has cellobiohydrolase activity.

In an embodiment, the variant has a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent cellobiohydrolase.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 4.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 5.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 6.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 7.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 8.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 9.

The present invention also provides cellobiohydrolase variants, comprising a variant catalytic domain, wherein the variant catalytic domain comprises a substitution at one or more positions corresponding to positions 201, 243, 286, and 343 of SEQ ID NO: 1, wherein the variant has cellobiohydrolase activity.

In an embodiment, the variant catalytic domain has a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the catalytic domain of a parent cellobiohydrolase.

In another embodiment, the variant catalytic domain has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the catalytic domain of SEQ ID NO: 1.

In another embodiment, the variant catalytic domain has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the catalytic domain of SEQ ID NO: 2.

In another embodiment, the variant catalytic domain has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the catalytic domain of SEQ ID NO: 3.

In another embodiment, the variant catalytic domain has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the catalytic domain of SEQ ID NO: 4.

In another embodiment, the variant catalytic domain has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the catalytic domain of SEQ ID NO: 5.

In another embodiment, the variant catalytic domain has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the catalytic domain of SEQ ID NO: 6.

In another embodiment, the variant catalytic domain has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the catalytic domain of SEQ ID NO: 7.

In another embodiment, the variant catalytic domain has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the catalytic domain of SEQ ID NO: 8.

In another embodiment, the variant catalytic domain has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the catalytic domain of SEQ ID NO: 9.

In one aspect, the number of substitutions in the variants of the present invention is 1-4, e.g., 1, 2, 3, or 4 substitutions.

In another aspect, the variant comprises a substitution at one or more (e.g., several) positions corresponding to positions 201, 243, 286, and 343. In another aspect, a variant comprises a substitution at two positions corresponding to any of positions 201, 243, 286, and 343. In another aspect, a variant comprises a substitution at three positions corresponding to any of positions 201, 243, 286, and 343. In another aspect, a variant comprises a substitution at each position corresponding to positions 201, 243, 286, and 343.

In another aspect, the variant comprises or consists of a substitution at a position corresponding to position 201. In another aspect, the amino acid at a position corresponding to position 201 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the variant comprises or consists of the substitution S201D of the polypeptide of SEQ ID NO: 1. In another aspect, the variant comprises or consists of the substitution S201D of the catalytic domain of SEQ ID NO: 1.

In another aspect, the variant comprises or consists of a substitution at a position corresponding to position 243. In another aspect, the amino acid at a position corresponding to position 243 is substituted with Ala, Arg, Asn, Asp, Cys, Gin, Glu, Gly, His, Ile, Lys, Met, Phe, Pro, Ser, Thr, Trp, Tyr, or Val, preferably with Glu, Lys, or Val, and more preferably with Val. In another aspect, the variant comprises or consists of the substitution L243E, L243K, or L243V of the polypeptide of SEQ ID NO: 1. In another aspect, the variant comprises or consists of the substitution L243E, L243K, or L243V of the catalytic domain of SEQ ID NO: 1.

In another aspect, the variant comprises or consists of a substitution at a position corresponding to position 286. In another aspect, the amino acid at a position corresponding to position 286 is substituted with Ala, Arg, Asn, Asp, Cys, Gin, Glu, Gly, His, Ile, Leu, Lys, Met, Phe, Pro, Ser, Thr, Trp, or Tyr, preferably with Ala. In another aspect, the variant comprises or consists of the substitution V286A of the polypeptide of SEQ ID NO: 1. In another aspect, the variant comprises or consists of the substitution V286A of the catalytic domain of SEQ ID NO: 1.

In another aspect, the variant comprises or consists of a substitution at a position corresponding to position 343. In another aspect, the amino acid at a position corresponding to position 343 is substituted with Ala, Arg, Asn, Asp, Cys, Gln, Glu, Gly, His, Ile, Leu, Lys, Met, Phe, Pro, Thr, Trp, Tyr, or Val, preferably with Glu or Gly. In another aspect, the variant comprises or consists of the substitution S343E,G of the polypeptide of SEQ ID NO: 1. In another aspect, the variant comprises or consists of the substitution S343E,G of the catalytic domain of SEQ ID NO: 1.

In another aspect, the variant comprises or consists of a substitution at positions corresponding to positions 201 and 243, such as those described above.

In another aspect, the variant comprises or consists of a substitution at positions corresponding to positions 201 and 286, such as those described above.

In another aspect, the variant comprises or consists of a substitution at positions corresponding to positions 201 and 343, such as those described above.

In another aspect, the variant comprises or consists of a substitution at positions corresponding to positions 243 and 286, such as those described above.

In another aspect, the variant comprises or consists of a substitution at positions corresponding to positions 243 and 343, such as those described above.

In another aspect, the variant comprises or consists of a substitution at positions corresponding to positions 286 and 343, such as those described above.

In another aspect, the variant comprises or consists of a substitution at positions corresponding to positions 201, 243, and 286, such as those described above.

In another aspect, the variant comprises or consists of a substitution at positions corresponding to positions 201, 243, and 343, such as those described above.

In another aspect, the variant comprises or consists of a substitution at positions corresponding to positions 201, 286, and 343, such as those described above.

In another aspect, the variant comprises or consists of a substitution at positions corresponding to positions 243, 286, and 343, such as those described above.

In another aspect, the variant comprises or consists of a substitution at positions corresponding to positions 201, 243, 286, and 343, such as those described above.

In another aspect, the variant comprises or consists of one or more (e.g., several) substitutions selected from the group consisting of S201D, L243E,K,V, V286A, and S343E,G at positions in SEQ ID NO: 1 or at positions corresponding to SEQ ID NO: 1 in other parent cellobiohydrolases, such as those described herein.

In another aspect, the variant comprises or consists of the substitutions S201D+L243E,K,V of the polypeptide of SEQ ID NO: 1 or the catalytic domain thereof.

In another aspect, the variant comprises or consists of the substitutions S201D+V286A of the polypeptide of SEQ ID NO: 1 or the catalytic domain thereof.

In another aspect, the variant comprises or consists of the substitutions S201D+S343E,G of the polypeptide of SEQ ID NO: 1 or the catalytic domain thereof.

In another aspect, the variant comprises or consists of the substitutions L243E,K,V+V286A of the polypeptide of SEQ ID NO: 1 or the catalytic domain thereof.

In another aspect, the variant comprises or consists of the substitutions L243E,K,V+S343E,G of the polypeptide of SEQ ID NO: 1 or the catalytic domain thereof.

In another aspect, the variant comprises or consists of the substitutions V286A+S343E,G of the polypeptide of SEQ ID NO: 1 or the catalytic domain thereof.

In another aspect, the variant comprises or consists of the substitutions S201D+L243E,K,V+V286A of the polypeptide of SEQ ID NO: 1 or the catalytic domain thereof.

In another aspect, the variant comprises or consists of the substitutions S201D+L243E,K,V+S343E,G of the polypeptide of SEQ ID NO: 1 or the catalytic domain thereof.

In another aspect, the variant comprises or consists of the substitutions S201D+V286A+S343E,G of the polypeptide of SEQ ID NO: 1 or the catalytic domain thereof.

In another aspect, the variant comprises or consists of the substitutions L243E,K,V+V286A+S343E,G of the polypeptide of SEQ ID NO: 1 or the catalytic domain thereof.

In another aspect, the variant comprises or consists of the substitutions S201D+L243E,K,V+V286A+S343E,G of the polypeptide of SEQ ID NO: 1 or the catalytic domain thereof.

The variants may further comprise one or more additional alterations, e.g., substitutions, insertions, or deletions at one or more (e.g., several) other positions.

In one aspect, the variant further comprises a substitution at one or more (e.g., several) positions corresponding to positions 101, 143, 186, 217, 236, 245, 250, 251, 289, 295, 311, 321, 327, 333, 365, 374, 429, and 441 of SEQ ID NO: 1, e.g., E101H, S186Y, A236S, C245L, T251K, N289D, D321N, Q327K, L333F, G365E, G374C, T429Q, and N441C.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellobiohydrolase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The variants may consist of 400 to 500, e.g., 400 to 450, 410 to 440, 415 to 435, and 420 to 440 amino acids.

In an embodiment, the variant has a foreign (heterologous) carbohydrate binding module (a carbohydrate binding module from a different parent).

In an embodiment, the variant has improved catalytic efficiency compared to the parent enzyme.

In an embodiment, the variant has improved catalytic rate compared to the parent enzyme.

In an embodiment, the variant has improved glucose tolerance.

Parent Cellobiohydrolases

The parent cellobiohydrolase may be any polypeptide having cellobiohydrolase activity.

The parent cellobiohydrolase may be a polypeptide having at least 60% sequence identity to the polypeptide of SEQ ID NO: 1, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have cellobiohydrolase activity. In one aspect, the amino acid sequence of the parent differs by up to 10 amino acids, e.g., 1, 2, 3, 4, 5, 6, 7, 8, 9, or 10, from the polypeptide of SEQ ID NO: 1.

The parent cellobiohydrolase may be a polypeptide having at least 60% sequence identity to the polypeptide of SEQ ID NO: 2, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by up to 10 amino acids, e.g., 1, 2, 3, 4, 5, 6, 7, 8, 9, or 10, from the polypeptide of SEQ ID NO: 2.

The parent cellobiohydrolase may be a polypeptide having at least 60% sequence identity to the polypeptide of SEQ ID NO: 3, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by up to 10 amino acids, e.g., 1, 2, 3, 4, 5, 6, 7, 8, 9, or 10, from the polypeptide of SEQ ID NO: 3.

The parent cellobiohydrolase may be a polypeptide having at least 60% sequence identity to the polypeptide of SEQ ID NO: 4, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by up to 10 amino acids, e.g., 1, 2, 3, 4, 5, 6, 7, 8, 9, or 10, from the polypeptide of SEQ ID NO: 4.

The parent cellobiohydrolase may be a polypeptide having at least 60% sequence identity to the polypeptide of SEQ ID NO: 5, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by up to 10 amino acids, e.g., 1, 2, 3, 4, 5, 6, 7, 8, 9, or 10, from the polypeptide of SEQ ID NO: 5.

The parent cellobiohydrolase may be a polypeptide having at least 60% sequence identity to the polypeptide of SEQ ID NO: 6, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by up to 10 amino acids, e.g., 1, 2, 3, 4, 5, 6, 7, 8, 9, or 10, from the polypeptide of SEQ ID NO: 6.

The parent cellobiohydrolase may be a polypeptide having at least 60% sequence identity to the polypeptide of SEQ ID NO: 7, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by up to 10 amino acids, e.g., 1, 2, 3, 4, 5, 6, 7, 8, 9, or 10, from the polypeptide of SEQ ID NO: 7.

The parent cellobiohydrolase may be a polypeptide having at least 60% sequence identity to the polypeptide of SEQ ID NO: 8, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by up to 10 amino acids, e.g., 1, 2, 3, 4, 5, 6, 7, 8, 9, or 10, from the polypeptide of SEQ ID NO: 8.

The parent cellobiohydrolase may be a polypeptide having at least 60% sequence identity to the polypeptide of SEQ ID NO: 9, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the parent differs by up to 10 amino acids, e.g., 1, 2, 3, 4, 5, 6, 7, 8, 9, or 10, from the polypeptide of SEQ ID NO: 9.

The catalytic domain of a parent cellobiohydrolase may be a catalytic domain having at least 60% sequence identity to the catalytic domain of SEQ ID NO: 1, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have cellobiohydrolase activity. In one aspect, the amino acid sequence of the catalytic domain of the parent differs by up to 10 amino acids, e.g., 1, 2, 3, 4, 5, 6, 7, 8, 9, or 10, from the catalytic domain of SEQ ID NO: 1.

The catalytic domain of a parent cellobiohydrolase may be a catalytic domain having at least 60% sequence identity to the catalytic domain of SEQ ID NO: 2, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the catalytic domain of the parent differs by up to 10 amino acids, e.g., 1, 2, 3, 4, 5, 6, 7, 8, 9, or 10, from the catalytic domain of SEQ ID NO: 2.

The catalytic domain of a parent cellobiohydrolase may be a catalytic domain having at least 60% sequence identity to the catalytic domain of SEQ ID NO: 3, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the catalytic domain of the parent differs by up to 10 amino acids, e.g., 1, 2, 3, 4, 5, 6, 7, 8, 9, or 10, from the catalytic domain of SEQ ID NO: 3.

The catalytic domain of a parent cellobiohydrolase may be a catalytic domain having at least 60% sequence identity to the catalytic domain of SEQ ID NO: 4, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the catalytic domain of the parent differs by up to 10 amino acids, e.g., 1, 2, 3, 4, 5, 6, 7, 8, 9, or 10, from the catalytic domain of SEQ ID NO: 4.

The catalytic domain of a parent cellobiohydrolase may be a catalytic domain having at least 60% sequence identity to the catalytic domain of SEQ ID NO: 5, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the catalytic domain of the parent differs by up to 10 amino acids, e.g., 1, 2, 3, 4, 5, 6, 7, 8, 9, or 10, from the catalytic domain of SEQ ID NO: 5.

The catalytic domain of a parent cellobiohydrolase may be a catalytic domain having at least 60% sequence identity to the catalytic domain of SEQ ID NO: 6, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the catalytic domain of the parent differs by up to 10 amino acids, e.g., 1, 2, 3, 4, 5, 6, 7, 8, 9, or 10, from the catalytic domain of SEQ ID NO: 6.

The catalytic domain of a parent cellobiohydrolase may be a catalytic domain having at least 60% sequence identity to the catalytic domain of SEQ ID NO: 7, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the catalytic domain of the parent differs by up to 10 amino acids, e.g., 1, 2, 3, 4, 5, 6, 7, 8, 9, or 10, from the catalytic domain of SEQ ID NO: 7.

The catalytic domain of a parent cellobiohydrolase may be a catalytic domain having at least 60% sequence identity to the catalytic domain of SEQ ID NO: 8, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the catalytic domain of the parent differs by up to 10 amino acids, e.g., 1, 2, 3, 4, 5, 6, 7, 8, 9, or 10, from the catalytic domain of SEQ ID NO: 8.

The catalytic domain of a parent cellobiohydrolase may be a catalytic domain having at least 60% sequence identity to the catalytic domain of SEQ ID NO: 9, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the amino acid sequence of the catalytic domain of the parent differs by up to 10 amino acids, e.g., 1, 2, 3, 4, 5, 6, 7, 8, 9, or 10, from the catalytic domain of SEQ ID NO: 9.

In another aspect, the parent comprises or consists of the amino acid sequence of SEQ ID NO: 1 or the catalytic domain thereof.

In another aspect, the parent comprises or consists of the amino acid sequence of SEQ ID NO: 2 or the catalytic domain thereof.

In another aspect, the parent comprises or consists of the amino acid sequence of SEQ ID NO: 3 or the catalytic domain thereof.

In another aspect, the parent comprises or consists of the amino acid sequence of SEQ ID NO: 4 or the catalytic domain thereof.

In another aspect, the parent comprises or consists of the amino acid sequence of SEQ ID NO: 5 or the catalytic domain thereof.

In another aspect, the parent comprises or consists of the amino acid sequence of SEQ ID NO: 6 or the catalytic domain thereof.

In another aspect, the parent comprises or consists of the amino acid sequence of SEQ ID NO: 7 or the catalytic domain thereof.

In another aspect, the parent comprises or consists of the amino acid sequence of SEQ ID NO: 8 or the catalytic domain thereof.

In another aspect, the parent comprises or consists of the amino acid sequence of SEQ ID NO: 9 or the catalytic domain thereof.

In another aspect, the parent is a fragment of the polypeptide of SEQ ID NO: 1, 2, 3, 4, 5, 6, 7, 8, or 9 containing at least 380 amino acid residues, e.g., at least 400 and at least 420 amino acid residues.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be a fungal cellobiohydrolase. For example, the parent may be a yeast cellobiohydrolase such as a *Candida*, *Kluyveromyces*, *Pichia*, *Saccharomyces*, *Schizosaccharomyces*, or *Yarrowia* cellobiohydrolase; or a filamentous fungal cellobiohydrolase such as an *Acremonium*, *Agaricus*, *Alternaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Dipodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* cellobiohydrolase.

In another aspect, the parent is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cellobiohydrolase.

In another aspect, the parent is an *Acremonium cellulolyticus*, *Aspergillus aculeatus*, *Aspergillus awamori*, *Aspergillus foetidus*, *Aspergillus fumigatus*, *Aspergillus japonicus*, *Aspergillus lentulus*, *Aspergillus nidulans*, *Aspergillus niger*, *Aspergillus oryzae*, *Aspergillus terreus*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Fennellia nivea*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium emersonii*, *Penicillium funiculosum*, *Penicillium pinophilum*, *Penicillium purpurogenum*, *Phanerochaete chrysosporium*, *Talaromyces emersonii*, *Talaromyces leycettanus*, *Thermoascus aurantiacus*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia setosa*, *Thielavia spededonium*, *Thielavia subthermophila*, *Thielavia terrestris*, *Trichoderma harzianum*, *Trichoderma koningii*, *Trichoderma longibrachiatum*, *Trichoderma reesei*, or *Trichoderma viride* cellobiohydrolase.

In another aspect, the parent is a *Talaromyces leycettanus* cellobiohydrolase, e.g., the cellobiohydrolase of SEQ ID NO: 1.

In another aspect, the parent is a *Trichoderma reesei* cellobiohydrolase, e.g., the cellobiohydrolase of SEQ ID NO: 2.

In another aspect, the parent is a *Fusarium solani* cellobiohydrolase, e.g., the cellobiohydrolase of SEQ ID NO: 3.

In another aspect, the parent is a *Myceliophthora thermophila* cellobiohydrolase, e.g., the cellobiohydrolase of SEQ ID NO: 4.

In another aspect, the parent is a cellobiohydrolase of SEQ ID NO: 5.

In another aspect, the parent is a cellobiohydrolase of SEQ ID NO: 6.

In another aspect, the parent is a cellobiohydrolase of SEQ ID NO: 7.

In another aspect, the parent is an *Aspergillus fumigatus* cellobiohydrolase, e.g., the cellobiohydrolase of SEQ ID NO: 8.

In another aspect, the parent is a cellobiohydrolase of SEQ ID NO: 9.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, *Molecular Cloning, A Laboratory Manual*, 2d edition, Cold Spring Harbor, N.Y.).

Preparation of Variants

The present invention also relates to methods for obtaining a variant having cellobiohydrolase activity, comprising: (a) introducing into a parent cellobiohydrolase a substitution at one or more (e.g., several) positions corresponding to positions 201, 243, 286, and 343 of the polypeptide of SEQ ID NO: 1, wherein the variant has cellobiohydrolase activity; and (b) recovering the variant.

In one aspect, the method further comprises introducing a substitution at one or more (e.g., several) positions corresponding to positions 101, 143, 186, 217, 236, 245, 250, 251, 289, 295, 311, 321, 327, 333, 365, 374, 429, and 441 of SEQ ID NO: 1, e.g., E101H, S186Y, A236S, C245L, T251K, N289D, D321N, Q327K, L333F, G365E, G374C, T429Q, and N441C.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent. Any site-directed mutagenesis procedure can be used in the present invention. There are many commercial kits available that can be used to prepare variants.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Site-saturation mutagenesis systematically replaces a polypeptide coding sequence with sequences encoding all 19 amino acids at one or more (e.g., several) specific positions (Parikh and Matsumura, 2005, *J. Mol. Biol.* 352: 621-628).

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide recognized by a host cell for expression of a polynucleotide encoding a variant of the present invention. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the variant. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active variant by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a variant and the signal peptide sequence is positioned next to the N-terminus of the propeptide sequence.

It may also be desirable to add regulatory sequences that regulate expression of the variant relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Talaromyces emersonii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising (a) cultivating a recombinant host cell of the present invention under conditions conducive for production of the variant; and optionally (b) recovering the variant.

The host cells are cultivated in a nutrient medium suitable for production of the variant using methods known in the art. For example, the cells may be cultivated by multi-well plates such as 24, 48, or 96 well plates, shake flask cultivation, or small-scale or large-scale fermentation (including continuous, batch, fed-batch, or solid state fermentations) in laboratory or industrial fermentors in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variants may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation. In one aspect, the whole fermentation broth is recovered.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant.

Fermentation Broth Formulations or Cell Compositions

The present invention also relates to a fermentation broth formulation or a cell composition comprising a variant of the present invention. The fermentation broth product further comprises additional ingredients used in the fermentation process, such as, for example, cells (including, the host cells containing the gene encoding the variant of the present invention which are used to produce the variant), cell debris, biomass, fermentation media and/or fermentation products. In some embodiments, the composition is a cell-killed whole broth containing organic acid(s), killed cells and/or cell debris, and culture medium.

The term "fermentation broth" refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, a cellulose induced protein (CIP), an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of uses of the compositions of the present invention. The dosage of the composition and other conditions under which the composition is used may be determined on the basis of methods known in the art.

Enzyme Compositions

The present invention also relates to compositions comprising a variant of the present invention. Preferably, the compositions are enriched in such a variant.

The compositions may comprise a variant of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, an AA9 polypeptide, a CIP, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of uses of the compositions of the present invention. The dosage of the composition and other conditions under which the composition is used may be determined on the basis of methods known in the art.

Examples are given below of preferred uses of the compositions of the present invention. The dosage of the composition and other conditions under which the composition is used may be determined on the basis of methods known in the art.

Uses

The present invention is also directed to the following processes for using the variants having cellobiohydrolase activity, or compositions thereof.

The present invention also relates to processes for degrading a cellulosic material, comprising: treating the cellulosic material with an enzyme composition comprising a variant having cellobiohydrolase activity of the present invention. In one aspect, the processes further comprise recovering the degraded cellulosic material. Soluble products from the degradation of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition comprising a variant having cellobiohydrolase activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition comprising a variant having cellobiohydrolase activity of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel (ethanol, n-butanol, isobutanol, biodiesel, jet fuel) and/or platform chemicals (e.g., acids, alcohols, ketones, gases, oils, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd et al., 2002, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment. The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, *Bioresource Technology* 855: 1-33; Schell et al., 2004, *Bioresource Technology* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, *Bioresource Technology* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic material with liquid or gaseous ammonia at moderate temperatures such as 90-150° C. and high pressure such as 17-bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt. %, e.g., 20-70 wt. % or 30-60 wt. %, such as around 40 wt. %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment.

The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by one or more enzyme compositions in one or more stages. The hydrolysis can be carried out as a batch process or series of batch processes. The hydrolysis can be carried out as a fed batch or continuous process, or series of fed batch or continuous processes, where the cellulosic material is fed gradually to, for example, a hydrolysis solution containing an enzyme composition. In an embodiment the saccharification is a continuous saccharification in which a cellulosic material and a cellulolytic enzyme composition are added at different intervals throughout the saccharification and the hydrolysate is removed at different intervals throughout the saccharification. The removal of the hydrolysate may occur prior to, simultaneously with, or after the addition of the cellulosic material and the cellulolytic enzyme composition.

Enzymatic hydrolysis is preferably carried out in a suitable aqueous environment under conditions that can be readily determined by one skilled in the art. In one aspect, hydrolysis is performed under conditions suitable for the activity of the enzymes(s), i.e., optimal for the enzyme(s).

The saccharification is generally performed in stirred-tank reactors or fermentors under controlled pH, temperature, and mixing conditions. Suitable process time, temperature and pH conditions can readily be determined by one skilled in the art. For example, the total saccharification time can last up to 200 hours, but is typically performed for preferably about 4 to about 120 hours, e.g., about 12 to about 96 hours or about 24 to about 72 hours. The temperature is in the range of preferably about 25° C. to about 80° C., e.g., about 30° C. to about 70° C., about 40° C. to about 60° C., or about 50° C. to about 55° C. The pH is in the range of preferably about 3 to about 9, e.g., about 3.5 to about 8, about 4 to about 7, about 4.2 to about 6, or about 4.3 to about 5.5.

The dry solids content is in the range of preferably about 5 to about 50 wt. %, e.g., about to about 40 wt. % or about 20 to about 30 wt. %.

In one aspect, the saccharification is performed in the presence of dissolved oxygen at a concentration of at least 0.5% of the saturation level.

In an embodiment of the invention the dissolved oxygen concentration during saccharification is in the range of at least 0.5% up to 30% of the saturation level, such as at least 1% up to 25%, at least 1% up to 20%, at least 1% up to 15%, at least 1% up to 10%, at least 1% up to 5%, and at least 1% up to 3% of the saturation level. In a preferred embodiment, the dissolved oxygen concentration is maintained at a concentration of at least 0.5% up to 30% of the saturation level, such as at least 1% up to 25%, at least 1% up to 20%, at least 1% up to 15%, at least 1% up to 10%, at least 1% up to 5%, and at least 1% up to 3% of the saturation level during at least 25% of the saccharification period, such as at least 50% or at least 75% of the saccharification period. When the enzyme composition comprises an oxidoreductase the dissolved oxygen concentration may be higher up to 70% of the saturation level.

Oxygen is added to the vessel in order to achieve the desired concentration of dissolved oxygen during saccharification. Maintaining the dissolved oxygen level within a desired range can be accomplished by aeration of the vessel, tank or the like by adding compressed air through a diffuser or sparger, or by other known methods of aeration. The aeration rate can be controlled on the basis of feedback from a dissolved oxygen sensor placed in the vessel/tank, or the system can run at a constant rate without feedback control. In the case of a hydrolysis train consisting of a plurality of vessels/tanks connected in series, aeration can be implemented in one or more or all of the vessels/tanks. Oxygen aeration systems are well known in the art. According to the invention any suitable aeration system may be used. Commercial aeration systems are designed by, e.g., Chemineer, Derby, England, and build by, e.g., Paul Mueller Company, Mo., USA.

The enzyme compositions can comprise any protein useful in degrading the cellulosic material.

In one aspect, the enzyme composition comprises or further comprises one or more (e.g., several) proteins selected from the group consisting of a cellulase, an AA9 polypeptide, a hemicellulase, an esterase, an expansin, a ligninolytic enzyme, an oxidoreductase, a pectinase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another aspect, the oxidoreductase is preferably one or more (e.g., several) enzymes selected from the group consisting of a catalase, a laccase, and a peroxidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises an AA9 polypeptide. In another aspect, the enzyme composition comprises an endoglucanase and an AA9 polypeptide. In another aspect, the enzyme composition comprises a cellobiohydrolase and an AA9 polypeptide. In another aspect, the enzyme composition comprises a beta-glucosidase and an AA9 polypeptide. In another aspect, the enzyme composition comprises an endoglucanase and a cellobiohydrolase. In another aspect, the enzyme composition comprises an endoglucanase I, an endoglucanase II, or a combination of an endoglucanase I and an endoglucanase II, and a cellobiohydrolase I, a cellobiohydrolase II, or a combination of a cellobiohydrolase I and a cellobiohydrolase II. In another aspect, the enzyme composition comprises an endoglucanase and a beta-glucosidase. In another aspect, the enzyme composition comprises an endoglucanase I, an endoglucanase II, or a combination of an endoglucanase I and an endoglucanase II, and a beta-glucosidase. In another aspect, the enzyme composition comprises a beta-glucosidase and a cellobiohydrolase. In another aspect, the enzyme composition comprises a beta-glucosidase and a cellobiohydrolase I, a cellobiohydrolase II, or a combination of a cellobiohydrolase I and a cellobiohydrolase II. In another aspect, the enzyme composition comprises an endoglucanase, an AA9 polypeptide, and a cellobiohydrolase. In another aspect, the enzyme composition comprises an endoglucanase I, an endoglucanase II, or a combination of an endoglucanase I and an endoglucanase II, an AA9 polypeptide, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and an AA9 polypeptide. In another aspect, the enzyme composition comprises a beta-glucosidase, an AA9 polypeptide, and a cellobiohydrolase. In another aspect, the enzyme composition comprises a beta-glucosidase, an AA9 polypeptide, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and a cellobiohydrolase. In another aspect, the enzyme composition comprises an endoglucanase I, an endoglucanase II, or a combination of an endoglucanase I and an endoglucanase II, a beta-glucosidase, and a cellobiohydrolase I, a cellobiohydrolase II, or a combination of a cellobiohydrolase I and a cellobiohydrolase II. In another aspect, the enzyme composition comprises an endoglucanase, a cellobiohydrolase, a beta-glucosidase, and an AA9 polypeptide. In another aspect, the enzyme composition comprises an endoglucanase I, an endoglucanase II, or a combination of an endoglucanase I and an endoglucanase II, a beta-glucosidase, an AA9 polypeptide, and a cellobiohydrolase I, a cellobiohydrolase II, or a combination of a cellobiohydrolase I and a cellobiohydrolase II.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In an embodiment, the xylanase is a Family 10 xylanase. In another embodiment, the xylanase is a Family 11 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a ligninolytic enzyme. In an embodiment, the ligninolytic enzyme is a manganese peroxidase. In another embodiment, the ligninolytic enzyme is a lignin peroxidase. In another embodiment, the ligninolytic enzyme is a $H_2O_2$-producing enzyme. In another aspect, the enzyme composition comprises a pectinase. In another aspect, the enzyme composition comprises an oxidoreductase. In an embodiment, the oxidoreductase is a catalase. In another embodiment, the oxidoreductase is a laccase. In another embodiment, the oxidoreductase is a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be native proteins, recombinant proteins, or a combination of native proteins and recombinant proteins. For example, one or more (e.g., several) components may be native proteins of a cell, which is used as a host cell to express recombinantly one or more (e.g., several) other components of the enzyme composition. It is understood herein that the recombinant proteins may be heterologous (e.g., foreign) and/or native to the host cell. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and variants having cellobiohydrolase activity depend on several factors including, but not limited to, the mixture of cellulolytic enzymes and/or hemicellulolytic enzymes, the cellulosic material, the concentration of cellulosic material, the pretreatment(s) of the cellulosic material, temperature, time, pH, and inclusion of a fermenting organism (e.g., for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of the variant having cellobiohydrolase activity to the cellulosic or hemicellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic or hemicellulosic material.

In another aspect, an effective amount of the variant having cellobiohydrolase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic or hemicellulosic material, e.g., AA9 polypeptides can be derived or obtained from any suitable origin, including, archaeal, bacterial, fungal, yeast, plant, or animal origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by, e.g., site-directed mutagenesis or shuffling.

Each polypeptide may be a bacterial polypeptide. For example, each polypeptide may be a Gram-positive bacterial polypeptide having enzyme activity, or a Gram-negative bacterial polypeptide having enzyme activity.

Each polypeptide may also be a fungal polypeptide, e.g., a yeast polypeptide or a filamentous fungal polypeptide.

Chemically modified or protein engineered mutants of polypeptides may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host can be a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLIC® CTec4 (Novozymes A/S), CELLUCLAST™ (Novozymes A/S), NOVOZYM™ 188 (Novozymes A/S), SPEZYME™ CP (Genencor Int.), ACCELLERASE™ TRIO (DuPont), FILTRASE® NL (DSM); METHAPLUS® S/L 100 (DSM), ROHAMENT™ 7069 W (Röhm GmbH), or ALTERNAFUEL® CMAX3™ (Dyadic International, Inc.). The cellulolytic enzyme preparation is added in an amount effective from about 0.001 to about 5.0 wt. % of solids, e.g., about 0.025 to about 4.0 wt. % of solids or about 0.005 to about 2.0 wt. % of solids.

Examples of bacterial endoglucanases that can be used in the processes of the present invention, include, but are not limited to, *Acidothermus cellulolyticus* endoglucanase (WO 91/05039; WO 93/15186; U.S. Pat. No. 5,275,944; WO 96/02551; U.S. Pat. No. 5,536,655; WO 00/70031; WO 05/093050), *Erwinia carotovara* endoglucanase (Saarilahti et al., 1990, *Gene* 90: 9-14), *Thermobifida fusca* endoglucanase III (WO 05/093050), and *Thermobifida fusca* endoglucanase V (WO 05/093050).

Examples of fungal endoglucanases that can be used in the present invention, include, but are not limited to, *Trichoderma reesei* endoglucanase I (Penttila et al., 1986, *Gene* 45: 253-263, *Trichoderma reesei* Cel7B endoglucanase I (GenBank:M15665), *Trichoderma reesei* endoglucanase II (Saloheimo et al., 1988, *Gene* 63:11-22), *Trichoderma reesei* Cel5A endoglucanase II (GenBank: M19373), *Trichoderma reesei* endoglucanase III (Okada et al., 1988, *Appl. Environ. Microbiol.* 64: 555-563, GenBank: AB003694), *Trichoderma reesei* endoglucanase V (Saloheimo et al., 1994, *Molecular Microbiology* 13: 219-228, GenBank:Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Fusarium oxysporum* endoglucanase (GenBank:L29381), *Humicola grisea* var. *thermoidea* endoglucanase (GenBank:AB003107), *Melanocarpus albomyces* endoglucanase (GenBank:MAL515703), *Neurospora crassa* endoglucanase (GenBank:XM_324477), *Humicola insolens* endoglucanase V, *Myceliophthora thermophila* CBS 117.65 endoglucanase, *Thermoascus aurantiacus* endoglucanase I (GenBank:AF487830), *Trichoderma reesei* strain No. VTT-D-80133 endoglucanase (GenBank: M15665), and *Penicillium pinophilum* endoglucanase (WO 2012/062220).

Examples of cellobiohydrolases useful in the present invention include, but are not limited to, *Aspergillus aculeatus* cellobiohydrolase II (WO 2011/059740), *Aspergillus fumigatus* cellobiohydrolase I (WO 2013/028928), *Aspergillus fumigatus* cellobiohydrolase II (WO 2013/028928), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Penicillium occitanis* cellobiohydrolase I (GenBank:AY690482), *Talaromyces emersonii* cellobiohydrolase I (GenBank:AF439936), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 02/095014), *Penicillium brasilianum* IBT 20888 (WO 2007/019442 and WO 2010/088387), *Thielavia terrestris* (WO 2011/035029), and *Trichophaea saccata* (WO 2007/019442).

Other useful endoglucanases, cellobiohydrolases, and beta-glucosidases are disclosed in numerous Glycosyl Hydrolase families using the classification according to Henrissat, 1991, *Biochem. J.* 280: 309-316, and Henrissat and Bairoch, 1996, *Biochem. J.* 316: 695-696.

In the processes of the present invention, any AA9 polypeptide can be used as a component of the enzyme composition.

Examples of AA9 polypeptides useful in the processes of the present invention include, but are not limited to, AA9 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290 and WO 2012/149344), *Myceliophthora thermophila* (WO 2009/085935, WO 2009/085859, WO 2009/085864, WO 2009/085868, and WO 2009/033071), *Aspergillus fumigatus* (WO 2010/138754), *Penicillium pinophilum* (WO 2011/005867), *Thermoascus* sp. (WO 2011/039319), *Penicillium* sp. (emersoni0 (WO 2011/041397 and WO 2012/000892), *Thermoascus crustaceous* (WO 2011/041504), *Aspergillus aculeatus* (WO 2012/030799), *Thermomyces lanuginosus* (WO 2012/113340, WO 2012/129699, WO 2012/130964, and WO 2012/129699), *Aurantiporus alborubescens* (WO 2012/122477), *Trichophaea saccata* (WO 2012/122477), *Penicillium thomii* (WO 2012/122477), *Talaromyces stipitatus* (WO 2012/135659), *Humicola insolens* (WO 2012/146171), *Malbranchea cinnamomea* (WO 2012/101206), *Talaromyces leycettanus* (WO 2012/101206), *Chaetomium thermophilum* (WO 2012/101206), *Talaromyces thermophilus* (WO 2012/129697 and WO 2012/130950), *Acrophialophora fusispora* (WO 2013/043910), and *Corynascus sepedonium* (WO 2013/043910).

In one aspect, the AA9 polypeptide is used in the presence of a soluble activating divalent metal cation according to WO 2008/151043 or WO 2012/122518, e.g., manganese or copper.

In another aspect, the AA9 polypeptide is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

In one aspect, such a compound is added at a molar ratio of the compound to glucosyl units of cellulose of about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described in WO 2012/021401, and the soluble contents thereof. A liquor for cellulolytic enhancement of an AA9 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and an AA9 polypeptide during hydrolysis of a cellulosic substrate by a cellulolytic enzyme preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK), ALTERNA FUEL 100P (Dyadic), and ALTERNA FUEL 200P (Dyadic).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thermomyces lanuginosus* (GeneSeqP: BAA22485), *Talaromyces thermophilus* (GeneSeqP: BAA22834), *Thielavia terrestris* NRRL 8126 (WO 2009/079210), and *Trichophaea saccata* (WO 2011/057083).

Examples of beta-xylosidases useful in the processes of the present invention include, but are not limited to, beta-xylosidases from *Neurospora crassa* (SwissProt:Q7SOW4), *Trichoderma reesei* (UniProtKB/TrEM BL: Q92458), *Talaromyces emersonii* (Swiss Prot: Q8X212), and *Talaromyces thermophilus* (GeneSeqP:BAA22816).

Examples of acetylxylan esterases useful in the processes of the present invention include, but are not limited to, acetylxylan esterases from *Aspergillus aculeatus* (WO 2010/108918), *Chaetomium globosum* (UniProt:Q2GWX4), *Chaetomium gracile* (GeneSeqP:AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt:q7s259), *Phaeosphaeria nodorum* (UniProt:Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt:A1D9T4), *Neurospora crassa* (UniProt:Q9HGR3),

*Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP: AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt: alcc12), *Aspergillus fumigatus* (SwissProt:Q4WW45), *Aspergillus niger* (UniProt:Q96WX9), *Aspergillus terreus* (Swiss Prot: Q0CJP9), *Humicola insolens* (WO 2010/014706), *Penicillium aurantiogriseum* (WO 2009/068565), *Talaromyces emersonii* (UniProt:Q8X211), and *Trichoderma reesei* (UniProt:Q99024).

Examples of oxidoreductases useful in the processes of the present invention include, but are not limited to, *Aspergillus lentilus* catalase, *Aspergillus fumigatus* catalase, *Aspergillus niger* catalase, *Aspergillus oryzae* catalase, *Humicola insolens* catalase, *Neurospora crassa* catalase, *Penicillium emersonii* catalase, *Scytalidium thermophilum* catalase, *Talaromyces stipitatus* catalase, *Thermoascus aurantiacus* catalase, *Coprinus cinereus* laccase, *Myceliophthora thermophila* laccase, *Polyporus pinsitus* laccase, *Pycnoporus cinnabarinus* laccase, *Rhizoctonia solani* laccase, *Streptomyces coelicolor* laccase, *Coprinus cinereus* peroxidase, Soy peroxidase, Royal palm peroxidase.

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, C A, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, N Y, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous.

Any suitable hydrolyzed cellulosic material can be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Yeast include strains of *Candida, Kluyveromyces,* and *Saccharomyces*, e.g., *Candida sonorensis, Kluyveromyces marxianus,* and *Saccharomyces cerevisiae*.

Examples of fermenting organisms that can ferment pentose sugars in their native state include bacterial and fungal organisms, such as some yeast. Xylose fermenting yeast include strains of *Candida*, preferably *C. sheatae* or *C. sonorensis*; and strains of *Pichia*, e.g., *P. stipitis*, such as *P. stipitis* CBS 5773. Pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum,* and *Zymomonas mobilis* (Philippidis, G. P., 1996, Cellulose bioconversion technology, in *Handbook on Bioethanol: Production and Utilization*, Wyman, C. E., ed., Taylor & Francis, Washington, D.C., 179-212).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis,* and *C. scehatae; Clostridium*, such as *C. acetobutylicum, C. thermocellum,* and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans,* and *K. fragilis; Schizosaccharomyces*, such as *S. pombe; Ther-*

*moanaerobacter*, such as *Thermoanaerobacter saccharolyticum*; and *Zymomonas*, such as *Zymomonas mobilis*.

Commercially available yeast suitable for ethanol production include, e.g., BIO-FERM® AFT and XR (Lallemand Specialities, Inc., USA), ETHANOL REDO yeast (Lesaffre et Compagnie, France), FALI® (AB Mauri Food Inc., USA), FERMIOL® (Rymco International AG, Denmark), GERT STRAND™ (Gert Strand AB, Sweden), and SUPERSTART™ and THERMOSACC® fresh yeast (Lallemand Specialities, Inc., USA).

In an aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, *Appl. Biochem. Biotechnol.* 39-40: 135-147; Ho et al., 1998, *Appl. Environ. Microbiol.* 64: 1852-1859; Kotter and Ciriacy, 1993, *Appl. Microbiol. Biotechnol.* 38: 776-783; Walfridsson et al., 1995, *Appl. Environ. Microbiol.* 61: 4184-4190; Kuyper et al., 2004, *FEMS Yeast Research* 4: 655-664; Beall et al., 1991, *Biotech. Bioeng.* 38: 296-303; Ingram et al., 1998, *Biotechnol. Bioeng.* 58: 204-214; Zhang et al., 1995, *Science* 267: 240-243; Deanda et al., 1996, *Appl. Environ. Microbiol.* 62: 4465-4470; WO 03/062430).

In one aspect, the fermenting organism comprises a polynucleotide encoding a polypeptide having cellobiohydrolase activity of the present invention.

In another aspect, the fermenting organism comprises one or more polynucleotides encoding one or more cellulolytic enzymes, hemicellulolytic enzymes, and accessory enzymes described herein.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g., pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide.

In one aspect, the fermentation product is an alcohol. The term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603.

In another aspect, the fermentation product is an alkane. The alkane may be an unbranched or a branched alkane. The alkane can be, but is not limited to, pentane, hexane, heptane, octane, nonane, decane, undecane, or dodecane.

In another aspect, the fermentation product is a cycloalkane. The cycloalkane can be, but is not limited to, cyclopentane, cyclohexane, cycloheptane, or cyclooctane.

In another aspect, the fermentation product is an alkene. The alkene may be an unbranched or a branched alkene. The alkene can be, but is not limited to, pentene, hexene, heptene, or octene.

In another aspect, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another aspect, the fermentation product is a gas. The gas can be, but is not limited to, methane, $H_2$, $CO_2$, or CO. See, for example, Kataoka et al., 1997, *Water Science and*

*Technology* 36(6-7): 41-47; and Gunaseelan, 1997, *Biomass and Bioenergy* 13(1-2): 83-114.

In another aspect, the fermentation product is isoprene.

In another aspect, the fermentation product is a ketone. The term "ketone" encompasses a substance that contains one or more ketone moieties. The ketone can be, but is not limited to, acetone.

In another aspect, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Plants

The present invention also relates to isolated plants, e.g., a transgenic plant, plant part, or plant cell, comprising a polynucleotide of the present invention so as to express and produce the variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed (Sticklen, 2008, *Nature Reviews* 9: 433-443). For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, roots, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germ plasm. In this way, the number of generations required to introgress one or more traits into a particular genetic background is minimized.

The present invention also relates to methods of producing a variant of the present invention comprising: (a) cultivating a transgenic plant, plant part, or a plant cell comprising a polynucleotide encoding the variant under conditions conducive for production of the variant; and optionally (b) recovering the variant.

The present invention is further described by the following examples that should not be construed as limiting the scope of the invention.

EXAMPLES

Media and Solutions

DOB+CSM-Leu plates were composed of 3.4 g of yeast nitrogen base without amino acids and ammonium sulfate, 0.68 g of CSM-Leu, 1 ml of 100 mM $CuSO_4 \cdot 5H_2O$, 20 ml of 0.5 M $K_2HPO_4$, 20 g of Bacto agar, and 950 ml of deionized water. Forty ml of a 50% glucose solution were added after the autoclaved medium was tempered to 55° C.

SOC medium was composed of 0.5 g of NaCl, 5 g of yeast extract, 20 g of tryptone, 10 ml of 250 mM KCl, and deionized water to 1 liter.

TBE buffer was composed of 10.8 g of Tris Base, 5 g of boric acid, 4 ml of 0.5 M EDTA pH 8, and deionized water to 1 liter.

TE Buffer was composed of 1 M Tris pH 8.0 and 0.5 M EDTA pH 8.0.

2XYT plates were composed of 16 g of tryptone, 10 g of yeast extract, 5 g of NaCl, 15 g of Bacto agar, and deionized water to 1 liter.

2XYT+Amp plates were composed of 2XYT agar supplemented with 100 µg of ampicillin per ml.

YPD medium was composed of 10 g of yeast extract, 20 g of Bacto peptone, 40 ml of 50% glucose, and deionized water to 1 liter.

TABLE 1

Primers used in the Examples below

Mutagenesis Primers

| Mutant Name | Amino Acid Mutation | Primer Name | Primer Sequence |
|---|---|---|---|
| A14-2 | L243E | TI_CBHII Fwd L243E | CAGAAGTGTGCTAATGCTCAGAGTGCTTACGAGGAGTGC ATCAACTAT (SEQ ID NO: 10) |

TABLE 1-continued

Primers used in the Examples below

| | | | |
|---|---|---|---|
| | | TI_CBHII Rev L243E | GTAAGCACTCTGAGCATTAGCACACTTCTG (SEQ ID NO: 11) |
| | V286A | TI_CBHII Fwd V286A | CTTAGCCCGGCCGCTCAACTCTTTGCTTCCGCCTACCAGA ATGCAAGC (SEQ ID NO: 12) |
| | | TI_CBHII Rev V286A | GGAAGCAAAGAGTTGAGCGGCCGGGCTAAG (SEQ ID NO: 13) |
| | S343E | TI_CBHII Fwd S343E | CTGGCTCCATTGCTTCAGCAACAGGGATGGGAGTCAGTT CACTTTATC (SEQ ID NO: 14) |
| | | TI_CBHII Rev S343E | CCATCCCTGTTGCTGAAGCAATGGAGCCAG (SEQ ID NO: 15) |
| A14-4 | L243K | TI_CBHII Fwd L243K | CAGAAGTGTGCTAATGCTCAGAGTGCTTACAAGGAGTGC ATCAACTAT (SEQ ID NO: 16) |
| | | TI_CBHII Rev L243K | GTAAGCACTCTGAGCATTAGCACACTTCTG (SEQ ID NO: 17) |
| | V286A | TI_CBHII Fwd V286A | CTTAGCCCGGCCGCTCAACTCTTTGCTTCCGCGTACCAG AATGCAAGC (SEQ ID NO: 18) |
| | | TI_CBHII Rev V286A | GGAAGCAAAGAGTTGAGCGGCCGGGCTAAG (SEQ ID NO: 19) |
| A14-6 | L243V | TI_CBHII Fwd L243V | CAGAAGTGTGCTAATGCTCAGAGTGCTTACGTGGAGTGC ATCAACTAT (SEQ ID NO: 20) |
| | | TI_CBHII Rev L243V | GTAAGCACTCTGAGCATTAGCACACTTCTG (SEQ ID NO: 21) |

Cloning Primers

| Primer Name | Primer Sequence |
|---|---|
| 1208418 | TTGCAGCCAAGATCTCTGCACAGCAAACCATGTGGGGTCA (SEQ ID NO: 22) |
| 1208420 | TAAATCATATTAATTAAGCTTTAGAAAGAGGGGTTGGCGT (SEQ ID NO: 23) |
| 1209353 | GCTATTTTCTAACAAAGCATCTTAGATTA (SEQ ID NO: 24) |
| 1209355 | GCTGATCCCCTCGTTTTCGGAAACGCTTTG (SEQ ID NO: 25) |
| 1209354 | GGTCCGTTAAGGTTAGAAGAAGGCTACTTT (SEQ ID NO: 26) |
| 1209356 | CCTATTCCGAAGTTCCTATTCTCTAGAAAG (SEQ ID NO: 27) |
| 1211892 | TTGCTATGTACATCGATGCTGGTCATGCTG (SEQ ID NO: 28) |
| 1211893 | CAGCATGACCAGCATCGATGTACATAGCAA (SEQ ID NO: 29) |
| 1211894 | GAGCAGAAATACATCAACGCTCTGGCTCCA (SEQ ID NO: 30) |
| 1211895 | TGGAGCCAGAGCGTTGATGTATTTCTGCTC (SEQ ID NO: 31) |

Example 1: Construction of Plasmid pGMEr188

Plasmid pGMEr188 is an expression plasmid for the cDNA of the native *Talaromyces leycettanus* CBH II gene. Such cDNA for the *T. leycettanus* CBH II gene was obtained by designing three 500 bp DNA fragments (G-blocks) with 5' and 3' homology with one another to facilitate the correct assembly of the gene cDNA. The sequence of the three G-blocks used are listed below and the regions in italics and underlined show the regions of homology between the DNA blocks:

G-block 1:
(SEQ ID NO: 32)
TGTAAGATCACCCTCTGTGTATTGCACCATGCGGTCTCTCCTGGCTCTTG
CCCCTACCCTGCTCGCGCCTGTTGTTCAGGCTCAGCAAACCATGTGGGGT
CAATGCGGTGGTCAGGGCTGGACCGGACCTACCATCTGTGTAGCAGGCGC
GACATGCAGCACACAGAACCCTTGGTATGCGCAGTGCACCCCAGCACCTA
CCGCGCCGACGACCTTGCAAACAACAACTACGACGAGCTCGAAATCGTCC
ACGACCACGAGCTCGAAGTCGTCCACGACCACAGGTGGAAGTGGCGGTGG -continued

```
AACTACGACCTCAACGTCAGCCACCATCACCGCGGCTCCATCTGGTAACC

CATACTCCGGATACCAGCTCTATGTGAACCAGGAATACTCGTCCGAGGTG

TACGCGTCTGCTATTCCTTCCCTTACCGGCACTCTGGTCGCGAAGGCAAG

CGCCGCGGCAGAGGTGCCATCTTTCCTGTGGCTGGACACTGCCTCCAAGG
```

G-block 2:

(SEQ ID NO: 33)

```
GAGGTGCCATCTTTCCTGTGGCTGGACACTGCCTCCAAGGTGCCACTGAT

GGGCACTTACTTGCAGGATATCCAGGCGAAGAACGCTGCTGGCGCCAACC

CACCATATGCCGGTCAATTCGTGGTTTACGACTTGCCGGATCGTGATTGC

GCTGCATTGGCCAGCAATGGAGAGTACTCCATTGCTAACAATGGTGTTGC

CAACTACAAGGCTTACATCGACTCCATCCGCGCGCTTCTTGTTCAATACT

CGAACGTCCATGTCATCCTTGTGATCGAGCCCGACAGCTTGGCCAACCTT

GTCACCAACCTGAATGTTCAGAAGTGTGCTAATGCTCAGAGTGCTTACCT

GGAGTGCATCAACTATGCCCTCACTCAGTTGAACCTCAAGAACGTTGCTA

TGTACATCGATGCTGGTCATGCTGGATGGCTCGGCTGGCCCGCCAACCTT

AGCCCGGCCGCTCAACTCTTTGCTTCCGTATACCAGAATGCAAGCTCCCC
```

G-block 3:

(SEQ ID NO: 34)

```
TGCTTCCGTATACCAGAATGCAAGCTCCCCAGCTGCCGTTCGCGGCCTGG

CAACCAACGTGGCCAACTATAATGCCTGGTCGATCGCCACTTGCCCATCT

TACACCCAAGGCGACCCCAACTGCGACGAGCAGAAATACATCAACGCTCT

GGCTCCATTGCTTCAGCAACAGGGATGGTCATCAGTTCACTTTATCACCG

ATACCGGCCGTAACGGTGTCCAGCCTACCAAGCAGAATGCCTGGGGTGAC

TGGTGCAACGTTATCGGAACCGGCTTCGGTGTCCGTCCCACCACCAACAC

TGGCGATCCATTGGAGGATGCTTTCGTCTGGGTCAAGCCTGGTGGTGAGA

GTGATGGTACTTCCAACTCCACTTCGCCTCGCTACGACGCCCACTGCGGT

TACAGTGATGCTCTTCAGCCTGCTCCTGAGGCTGGTACCTGGTTCGAGGC

TTACTTTGAGCAACTCCTTA
```
CCAACGCCAACCCCTCTTTCTAATAGTTAA

The sequences highlighted in bold at the beginning of G-block 1 and at the end of G-block 3 indicate homology with the sense PCR primer 1203966 and the antisense PCR primer 1203967 shown below used in the G-block assembly reaction:

Primer 1203966 (sense):

(SEQ ID NO: 35)

5'-GCAGCTCACCTGAAGAGGCTTGTAAGATCACCCTCTGTGTATTGCA CC-3'

Primer 1203967 (antisense):

(SEQ ID NO: 36)

5'-CCAACGCCAACCCCTCTTTCTAATAGTTAATTAAGGCTTTCGTGACC GG-3'

The three G-blocks were synthesized by Integrated DNA Technologies, Inc. (Coralville, Iowa, USA), and were received as dry DNA fragments. The 500 bp G-block 1, the 500 bp G-block 2 and the 500 bp G-block 3 were assembled together by PCR using primer 1203966 (sense) and primer 1203967 (antisense), resulting in a 1469 bp fragment comprising the entire cDNA for the T. leycettanus CBH H gene. The PCR (50 μl) was composed of an equimolecular ratio of the three G-block fragments for a total amount of DNA of approximately 120 ng, 1× PHUSION® HF buffer (Thermo-Fisher Scientific), 50 pmol of primer 1203967, 50 pmol of primer 1203966, 200 μM each of dATP, dCTP, dGTP, and dTTP, 1.5 μl of 100% DMSO, and 1 unit of PHUSION® High Fidelity DNA polymerase (ThermoFisher Scientific). The reaction was performed in a thermocycler programmed for 1 cycle at 98° C. for 5 minutes; 35 cycles each at 98° C. for 30 seconds, 60° C. for 30 seconds, and 72° C. for 2 minutes and 30 seconds; and a final extension cycle at 72° C. for 7 minutes. The completed PCR was submitted to 0.8% agarose gel electrophoresis in TBE buffer where an approximately 1469 bp PCR product was excised from the gel and purified using a NUCLEOSPIN® Extract II Gel and PCR Clean-up Kit (Macherey-Nagel).

The resulting 1469 bp fragment, comprising the complete T. leycettanus native CBH II cDNA, was cloned after PCR and gel purification into plasmid PCR®4-Blunt TOPO® (Life Technologies Corp.) and transformed into ONE SHOT® TOP10 E. coli chemically competent cells (Invitrogen Corp.) by addition to a single use tube containing the competent cells and incubating the cells on ice for 5 minutes. The tube was incubated at 42° C. for 30 seconds after which 250 μl of SOC medium were added. The tube was then incubated at 37° C. with agitation at 200 rpm for 1 hour and 250 μl were transferred to 2XYT+amp plates and incubated at 37° C. overnight. Several of the resulting transformants were screened for proper insertion of the desired fragment by sequencing analysis. One transformant containing the correct plasmid was identified and the plasmid was designated pGMEr186.

The T. leycettanus CBH II cDNA was amplified by PCR from plasmid pGMEr186 using primer 1203966 (sense) and primer 1203967 (antisense). The PCR (50 μl) was composed of an equimolecular ratio of about 100 ng of plasmid pGMEr186, 1× PHUSION® HF buffer, 50 pmol of primer 1203966, 50 pmol of primer 1203967, 200 μM each of dATP, dCTP, dGTP, and dTTP, 1.5 μl of 100% DMSO, and 1 unit of PHUSION® High Fidelity DNA polymerase. The reaction was performed in a thermocycler programmed for 1 cycle at 98° C. for 5 minutes; 35 cycles each at 98° C. for 30 seconds, 60° C. for 30 seconds, and 72° C. for 50 seconds; and a final extension cycle at 72° C. for 7 minutes. The completed PCR was submitted to 0.8% agarose gel electrophoresis in TBE buffer where an approximately 1469 bp PCR product was excised from the gel and purified using a NUCLEOSPIN® Extract II Gel and PCR Clean-up Kit.

The resulting 1469 bp PCR fragment (T. leycettanus CBH II cDNA) was inserted into Nco I/Pac I-linearized plasmid pJfyS142 (WO 2013/028912) using an IN-FUSION® Advantage PCR Cloning Kit (Clontech Laboratories, Inc.). The reaction was composed of 1× IN-FUSION® Reaction Buffer, 50 ng of Nco I/Pac I-linearized pJfyS142, 100 ng of the T. leycettanus cbh II cDNA fragment (1469 bp), and 1 μl of IN-FUSION® Enzyme (Clontech Laboratories, Inc.) in a 10 μl reaction volume. The reaction was incubated for 15 minutes at 50° C. Then 40 μl of TE were added to the reaction and a 2 μl aliquot of the reaction was transformed into ONE SHOT® TOP10 E. coli chemically competent cells and transformants selected as described above. Several of the resulting transformants were screened for proper insertion of the desired fragment by Sac I restriction digestion. Plasmid DNA was extracted and purified using a Plasmid Mini Kit (QIAGEN Inc.). A transformant containing a plasmid yielding the desired band sizes of 4223 bp, 3912 bp, 2717 bp, 874 bp and 24 bp was isolated and the plasmid was designated pGMEr188.

Example 2: Construction of Yeast Expression Plasmid pLSBF103

Plasmid pLSBF103 was constructed for expression of the *Talaromyces leycettanus* CBH II (SEQ ID NO: 1) and generation of mutant gene libraries. The *Talaromyces leycettanus* CBH II cDNA coding sequence (WO 2012/103288) was amplified from plasmid pGMER188 (Example 1) using the primers shown in Table 1. Bold letters represent coding sequence. The remaining sequences are homologous to insertion sites of pLSBF101. Plasmid pLSBF101 was made by modifying plasmid pDB4081 (WO 2014/072481) to remove the sequence between the promoter and terminator and insert a *Saccharomyces cerevisiae* invertase leader sequence shown below followed by a Hind III restriction site.

```
                                           (SEQ ID NO: 37)
ATGCTTTTGCAAGCCTTCCTTTTCCTTTTGGCTGGTTTTGCAGCCAAGAT
CTCTGCA
```

Plasmid pLSBF101 was digested with Hind III to linearize the plasmid. The homologous ends of the PCR product and the digested pLSBF101 were joined together using an IN-FUSION™ Advantage PCR Cloning Kit and transformed into STELLAR™ competent *E. coli* cells (Clontech Laboratories, Inc.). Plasmid DNA was purified from transformed colonies using a QIAPREP® Spin Miniprep Kit (QIAGEN Inc.). DNA sequencing with a 3130XL Genetic Analyzer (Applied Biosystems, Inc.) confirmed the presence of the CBH II fragment in a final plasmid designated pLSBF103.

Example 3: Construction of *Talaromyces Leycettanus* CBH II Variants

*Talaromyces leycettanus* CBH II mutant libraries were constructed using a targeted mutagenesis approach. Mutagenic forward primers and complementary reverse primers were synthesized for each of the mutations of interest. Multiple PCR products were used in a yeast-assembly method to construct each mutant. Using plasmid pLSBF103 (Example 2) as a DNA template, mutations were introduced via PCR using the forward mutagenic primer for each mutation and a reverse primer downstream of the terminator (SEQ ID NO: 25—Primer 1209355). This reaction results in a PCR product containing a 3' fragment of the *Talaromyces leycettanus* CBH II gene containing the mutation of interest, a *Saccharomyces cerevisiae* alcohol dehydrogenase (ADH1) terminator, and a small amount of DNA necessary for yeast assembly during the transformation. A second PCR was performed using plasmid pLSBF103 as a DNA template with the non-mutagenic complementary reverse primer for each mutation and a forward primer upstream of the selectable marker (SEQ ID NO: 24—Primer 1209353). This reaction results in a PCR product containing a small amount of DNA necessary for yeast assembly during the transformation, a *Saccharomyces cerevisiae* 3-isopropylmalate dehydrogenase (LEU2) selectable marker gene, a *Saccharomyces cerevisiae* protease B (PRB1) promoter, a *Saccharomyces cerevisiae* invertase leader sequence, and a 5' fragment of the *Talaromyces leycettanus* CBH II gene. The two products were then pooled and used in a Splicing by Overlap Extension (SOE) PCR with a nested primer set (SEQ ID NOs: 26 and 27—Primers 1209354 and 1209356) to assemble them into one fragment. When co-transformed alongside linearized plasmid pDB4164 the two DNA fragments come together to form a complete 2 micron expression plasmid containing a *Talaromyces leycettanus* CBH II gene mutant. Plasmid pDB4164 was constructed by modifying plasmid pDB3936 (WO 2010/092135). It has two additional bases (GC) next to the BamH I site to create a Not I restriction site GCGGCCGC (additional bases in bold) and contains a 1368 bp sequence between the Acc 65I and BamH I sites containing an apramycin resistance selectable marker.

For variants with multiple mutations a similar procedure was followed. The following steps were used in the construction of mutant A14-4. In order to generate the right side fragment a PCR was performed using a V286A CBH II mutant as template with the original downstream reverse primer (SEQ ID NO: 25—Primer 1209355) and a new forward primer just upstream of position 286 (SEQ ID NO: 28—Primer 1211892). A left side fragment was generated through PCR using a L243K CBH II mutant as template with the original upstream forward primer (SEQ ID NO: 24—Primer 1209353) and a new reverse primer just downstream of position 243 which is complementary to the forward primer used in the right side PCR (SEQ ID NO: 29—Primer 1211893). Following amplification of the right and left side fragments the two products were pooled and used in a SOE PCR with a nested primer set (SEQ ID NOs: 26 and 27—Primers 1209354 and 1209356) to assemble them into one fragment. When co-transformed alongside linearized pDB4164 the two DNA fragments came together to form a complete 2 micron expression plasmid containing a *Talaromyces leycettanus* CBH II gene with mutations L243K and V286A incorporated.

The following steps were used in the construction of mutant A14-2. In order to generate the right side fragment a PCR was performed using a S343E CBH II mutant as template with the original downstream reverse primer (SEQ ID NO: 25—Primer 1209355) and a new forward primer just upstream of position 343 (SEQ ID NO: 30—Primer 1211894). A left side fragment was generated through PCR using a CBH II mutant containing L243E and V286A as template with the original upstream forward primer (SEQ ID NO: 24—Primer 1209353) and a new reverse primer just downstream of position 286 which is complementary to the forward primer used in the Right side PCR (SEQ ID NO: 31—Primer 1211895). Following amplification of the right and left side fragments the two products were pooled and used in a SOE PCR with a nested primer set (SEQ ID NOs: 26 and 27—Primers 1209354 and 1209356) to assemble them into one fragment. When co-transformed alongside linearized pDB4164 the two DNA fragments came together to form a complete 2 micron expression plasmid containing a *Talaromyces leycettanus* CBH II gene with mutations L243E, V286A, and S343E incorporated.

Example 4: Transformation and Expression of Variants in Yeast Host Strain

Plasmid pDB4164 DNA was prepared for transformation into *S. cerevisiae* as described in WO 2015/036579, Method 4, except that a 9723 bp Acc 65I-BamH I fragment from pDB4164 was used as the gapped vector fragment instead of the 9721 bp fragment from pDB3936, which has two additional bases GC next to the BamH I site to create a Not 1 restriction site GCGGCCGC. Plasmid pDB4164 also differs from pDB3936 in containing a 1368 bp sequence between the Acc 65I and BamH 1 sites containing an apramycin resistance selectable marker which was excised by the Acc 65I and BamH 1 digestion and was not used in the gap-repair transformation. Digested pDB4164 was co-transformed with a PCR product encoding either wild-type or mutated *Talaromyces leycettanus* CBH II. A *Saccharomyces cerevisiae* strain (as described in WO 2014/072481) was used as an expression host for the *Talaromyces leycettanus* CBH II variants. This strain was made from DYB7 (Payne et al., 2008, *Applied and Environmental Microbiology* 74(24): 7759-7766) with four copies of a protein disulfide isomerase integrated into the genome.

Transformed cells were plated onto a selective medium (DOB+CSM-Leu) and allowed to grow at 30° C. for several days. Following the outgrowth, the transformants were cultured in shake flasks to generate enough material for purification. A loop full of cells for each transformant was re-suspended in 15 μL of culture medium and used as inoculum. The cells were placed in a 1 L baffled glass shake flask with 200 mL of YPD medium+100 μM ampicillin and incubated at 30° C. on a 250 rpm shaker for 5 days. Following incubation, the cells were pelleted and the broths were filter sterilized.

Example 5: Purification of *Talaromyces leycettanus* CBH II Variants Expressed in Yeast Each broth (Example 4) was mixed with ½ volume of 20 mM Tris-HCl pH 7.5 containing 3.0 M ammonium sulfate to give a final concentration of 1.0 M ammonium sulfate and then filtered using a 0.22 μm polyethersulfone membrane (Millipore) to remove particulates. Each filtered sample was applied to a 75 mL Phenyl Sepharose HP column (GE Healthcare) equilibrated with 1.0 M ammonium sulfate in 20 mM Tris-HCl pH 7.5. Bound proteins were eluted with a decreasing salt gradient (10 column volumes) 1.0 M ammonium sulfate to 0 M ammonium sulfate in 20 mM Tris-HCl pH 7.5 with 10 mL fractions collected. Fractions were examined by SDS-PAGE using 8-16% CRITERION™ TGX Stain-Free™ SDS-PAGE gels (Bio-Rad Laboratories, Inc.). Each of the variants eluted at ~400 mM ammonium sulfate concentration during the gradient. Fractions containing variant were pooled and were >90% pure as judged by SDS-PAGE. Each pooled material was buffer exchanged into 50 mM sodium acetate pH 5, 100 mM NaCl using four HiPrep™ 26/10 desalting columns (GE Healthcare) linked in series. Protein concentration was determined by measuring the absorbance at 280 nm and using the calculated extinction coefficient of 2.078 (where a 1 mg/mL solution of the protein would have an absorbance at 280 nm of 2.078).

Example 6: Characterization of *Talaromyces leycettanus* GH6 CBH II Variants PCB+Glc Cane bagasse was pretreated using low acid steam explosion technique. Prior to enzymatic hydrolysis, the pretreated cane bagasse (PCB) was ground using a COSMOS® Multi Utility Grinder (EssEmm Corporation), and then was sieved through a 420 micron sieve. The dry content of the ground and sieved PCB was adjusted to 6.25%, glucose was added to the substrate to a concentration of 50 g/L, and the glucose-enriched pretreated cane bagasse (PCB) was autoclaved at 121° C. for 30 minutes. Fluorescent brightener 28 (Sigma-Aldrich, CAS #4404-43-7) was added to the substrate to reach 150 μM in the prepared substrate.

An Enzyme Composition without GH6 Cellobiohydrolase II

A synthetic enzyme mixture was used as base enzyme, including 49.3% *Talaromyces leycettanus* GH7 cellobiohydrolase 1, 13.3% *Thermoascus aurantiacus* GH5 endoglucanase 2, 20% *Thermomyces lanuginosus* GH61A polypeptide, 6.7% *Trichophaea saccata* GH10 xylanase, 6.7% *Aspergillus fumigatus* beta-glucosidase variant, and 4% *Talaromyces emersonii* beta-xylosidase. The enzyme composition is designated herein as "cellulolytic enzyme composition without cellobiohydrolase II".

All the components used here were at least desalted and buffer-exchanged into 50 mM sodium acetate pH 5.0 buffer using a HIPREP® 26/10 Desalting Column (GE Healthcare), or were further purified through Hydrophobic Interaction Chromatography (HIC) or Ion Exchange Chromatography (IEC) (GE Healthcare). The protein concentration was determined using a Microplate BCA™ Protein Assay Kit (Thermo Fischer Scientific) in which bovine serum albumin was used as a protein standard.

Hydrolysis of PCB+Glc

Hydrolysis of PCB+Glc (glucose-enriched pretreated cane bagasse (PCB)) was performed using the cellulolytic enzyme composition without cellobiohydrolase II at 2.0 mg enzyme/g total solids, supplemented by a *Talaromyces leycettanus* CBH II variant or *Talaromyces leycettanus* wild-type CBH II at 0, 0.1, 0.2, 0.3, 0.4, 0.5, 0.6, 0.7 mg enzyme/g total solids, at 55° C., pH 5.0. Total insoluble solids loading of the glucose-enriched PCB was 50 g/L. The glucose concentration was 40 g/L in the hydrolysis reaction mixture. Total reaction volume was 0.25 ml in 96-well plates (Fisher Scientific). Assays were run in triplicate. After 72-hour incubation at 55° C., the plates were removed from the incubator, cooled down to room temperature, mixed thoroughly, and read on fluorescence plate reader (Molecular Devices, SpectraMax M5) with bottom read mode, excitation at 365 nm, emittance at 465 nm. The degree of cellulose conversion was calculated using the following equation, by the fluorescent readings of:

% Conversion=(Sub Ctrl−Reaction)/(Sub Ctrl−Max Digestion)*100%

Several *Talaromyces leycettanus* CBH II variants showed better performance than *Talaromyces leycettanus* wild-type CBH II at 55° C., pH 5.0. Table 2 shows that in the hydrolysis of PCB+Glc, *Talaromyces leycettanus* CBH II variants A14-2, A14-4 and A14-6, outperformed *Talaromyces leycettanus* wild type CBH II at 55° C., pH 5.0.

TABLE 2

Conversion by CBH IIs in hydrolysis of PCB + Glc, 55° C., pH 5.0.

| CBH II loading, mg/g TS | Talaromyces leycettanus wild-type CBH II | Talaromyces leycettanus CBH II variant A14-2 | Talaromyces leycettanus CBH II variant A14-4 | Talaromyces leycettanus CBH II variant A14-6 |
|---|---|---|---|---|
| 0   | 0%  | −1% | 0%  | 0%  |
| 0.1 | 9%  | 10% | 10% | 10% |
| 0.2 | 11% | 14% | 14% | 14% |
| 0.3 | 14% | 18% | 18% | 18% |
| 0.4 | 17% | 20% | 20% | 20% |
| 0.5 | 19% | 23% | 21% | 21% |
| 0.6 | 21% | 24% | 22% | 23% |
| 0.7 | 21% | 26% | 23% | 24% |

The present invention is further described by the following numbered paragraphs:

[Paragraph 1] A cellobiohydrolase variant, comprising a substitution at one or more positions corresponding to positions 201, 243, 286, and 343 of the polypeptide of SEQ ID NO: 1, wherein the variant has cellobiohydrolase activity and wherein the variant has at least 60%, e.g., at least 65%, at least 70%, at least 75%, at least 80%, at least 85%, at least 90%, at least 95%, at least 96%, at least 97%, at least 98%, or at least 99%, but less than 100%, sequence identity to a parent cellobiohydrolase.

[Paragraph 2] The cellobiohydrolase variant of paragraph 1, wherein the parent cellobiohydrolase has at least 60%, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 1, 2, 3, 4, 5, 6, 7, 8, or 9.

[Paragraph 3] The cellobiohydrolase variant of paragraph 1, wherein the parent cellobiohydrolase comprises or consists of SEQ ID NO: 1, 2, 3, 4, 5, 6, 7, 8, or 9.

[Paragraph 4] The cellobiohydrolase variant of paragraph 1, wherein the parent cellobiohydrolase is a fragment of SEQ ID NO: 1, 2, 3, 4, 5, 6, 7, 8, or 9, wherein the fragment has cellobiohydrolase activity.

[Paragraph 5] The cellobiohydrolase variant of paragraph 4, wherein the fragment consists of at least 85% of the amino acid residues, e.g., at least 90% of the amino acid residues or at least 95% of the amino acid residues of SEQ ID NO: 1, 2, 3, 4, 5, 6, 7, 8, or 9.

[Paragraph 6] The cellobiohydrolase variant of any one of paragraphs 1-5, which has at least 60%, e.g., at least 65%, at least 70%, at least 75%, at least 80%, at least 85%, at least 90%, at least 95%, at least 96%, at least 97%, at least 98%, or at least 99%, but less than 100%, sequence identity to the polypeptide of SEQ ID NO: 1, 2, 3, 4, 5, 6, 7, 8, or 9.

[Paragraph 7] The cellobiohydrolase variant of any one of paragraphs 1-6, which has at least 60%, e.g., at least 65%, at least 70%, at least 75%, at least 80%, at least 85%, at least 90%, at least 95%, at least 96%, at least 97%, at least 98%, or at least 99%, but less than 100%, sequence identity to the polypeptide of SEQ ID NO: 1.

[Paragraph 8] The cellobiohydrolase variant of any one of paragraphs 1-6, which has at least 60%, e.g., at least 65%, at least 70%, at least 75%, at least 80%, at least 85%, at least 90%, at least 95%, at least 96%, at least 97%, at least 98%, or at least 99%, but less than 100%, sequence identity to the polypeptide of SEQ ID NO: 2.

[Paragraph 9] The cellobiohydrolase variant of any one of paragraphs 1-6, which has at least 60%, e.g., at least 65%, at least 70%, at least 75%, at least 80%, at least 85%, at least 90%, at least 95%, at least 96%, at least 97%, at least 98%, or at least 99%, but less than 100%, sequence identity to the polypeptide of SEQ ID NO: 3.

[Paragraph 10] The cellobiohydrolase variant of any one of paragraphs 1-6, which has at least 60%, e.g., at least 65%, at least 70%, at least 75%, at least 80%, at least 85%, at least 90%, at least 95%, at least 96%, at least 97%, at least 98%, or at least 99%, but less than 100%, sequence identity to the polypeptide of SEQ ID NO: 4.

[Paragraph 11] The cellobiohydrolase variant of any one of paragraphs 1-6, which has at least 60%, e.g., at least 65%, at least 70%, at least 75%, at least 80%, at least 85%, at least 90%, at least 95%, at least 96%, at least 97%, at least 98%, or at least 99%, but less than 100%, sequence identity to the polypeptide of SEQ ID NO: 5.

[Paragraph 12] The cellobiohydrolase variant of any one of paragraphs 1-6, which has at least 60%, e.g., at least 65%, at least 70%, at least 75%, at least 80%, at least 85%, at least 90%, at least 95%, at least 96%, at least 97%, at least 98%, or at least 99%, but less than 100%, sequence identity to the polypeptide of SEQ ID NO: 6.

[Paragraph 13] The cellobiohydrolase variant of any one of paragraphs 1-6, which has at least 60%, e.g., at least 65%, at least 70%, at least 75%, at least 80%, at least 85%, at least 90%, at least 95%, at least 96%, at least 97%, at least 98%, or at least 99%, but less than 100%, sequence identity to the polypeptide of SEQ ID NO: 7.

[Paragraph 14] The cellobiohydrolase variant of any one of paragraphs 1-6, which has at least 60%, e.g., at least 65%, at least 70%, at least 75%, at least 80%, at least 85%, at least 90%, at least 95%, at least 96%, at least 97%, at least 98%, or at least 99%, but less than 100%, sequence identity to the polypeptide of SEQ ID NO: 8.

[Paragraph 15] The cellobiohydrolase variant of any one of paragraphs 1-6, which has at least 60%, e.g., at least 65%, at least 70%, at least 75%, at least 80%, at least 85%, at least 90%, at least 95%, at least 96%, at least 97%, at least 98%, or at least 99%, but less than 100%, sequence identity to the polypeptide of SEQ ID NO: 9.

[Paragraph 16] The cellobiohydrolase variant of any one of paragraphs 1-15, wherein the variant consists of 400 to 500, e.g., 400 to 450, 410 to 440, 415 to 435, and 420 to 440 amino acids.

[Paragraph 17] A cellobiohydrolase variant, comprising a variant catalytic domain, wherein the variant catalytic domain comprises a substitution at one or more positions corresponding to positions 201, 243, 286, and 343 of SEQ ID NO: 1 and has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the catalytic domain of a parent cellobiohydrolase.

[Paragraph 18] The cellobiohydrolase variant of paragraph 17, wherein the catalytic domain of the parent cellobiohydrolase has at least 60%, e.g., at least 65%, at least 70%, at least 75%, at least 80%, at least 85%, at least 90%, at least 95%, at least 96%, at least 97%, at least 98%, at least 99%, or 100% sequence identity to the catalytic domain of SEQ ID NO: 1, 2, 3, 4, 5, 6, 7, 8, or 9.

[Paragraph 19] The cellobiohydrolase variant of paragraph 17, wherein the catalytic domain of the parent cellobiohydrolase comprises or consists of the catalytic domain of SEQ ID NO: 1, 2, 3, 4, 5, 6, 7, 8, or 9.

[Paragraph 20] The cellobiohydrolase variant of paragraph 17, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the catalytic domain of SEQ ID NO: 1.

[Paragraph 21] The cellobiohydrolase variant of paragraph 17, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the catalytic domain of SEQ ID NO: 2.

[Paragraph 22] The cellobiohydrolase variant of paragraph 17, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the catalytic domain of SEQ ID NO: 3.

[Paragraph 23] The cellobiohydrolase variant of paragraph 17, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the catalytic domain of SEQ ID NO: 4.

[Paragraph 24] The cellobiohydrolase variant of paragraph 17, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the catalytic domain of SEQ ID NO: 5.

[Paragraph 25] The cellobiohydrolase variant of paragraph 17, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the catalytic domain of SEQ ID NO: 6.

[Paragraph 26] The cellobiohydrolase variant of paragraph 17, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the catalytic domain of SEQ ID NO: 7.

[Paragraph 27] The cellobiohydrolase variant of paragraph 17, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the catalytic domain of SEQ ID NO: 8.

[Paragraph 28] The cellobiohydrolase variant of paragraph 17, wherein the variant catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the catalytic domain of SEQ ID NO: 9.

[Paragraph 29] The cellobiohydrolase variant of any one of paragraphs 17-28, which further comprises a carbohydrate binding module.

[Paragraph 30] The cellobiohydrolase variant of paragraph 29, wherein the carbohydrate binding module is a foreign carbohydrate binding module.

[Paragraph 31] The cellobiohydrolase variant of any one of paragraphs 1-30, wherein the variant has 1-4, e.g., 1, 2, 3, or 4 substitutions.

[Paragraph 32] The cellobiohydrolase variant of any one of paragraphs 1-31, which comprises a substitution at a position corresponding to position 201 of SEQ ID NO: 1.

[Paragraph 33] The cellobiohydrolase variant of paragraph 32, wherein the substitution is with Asp.

[Paragraph 34] The cellobiohydrolase variant of any one of paragraphs 1-33, which comprises a substitution at a position corresponding to position 243 of SEQ ID NO: 1.

[Paragraph 35] The cellobiohydrolase variant of paragraph 34, wherein the substitution is with Glu, Lys, or Val.

[Paragraph 36] The cellobiohydrolase variant of any one of paragraphs 1-35, which comprises a substitution at a position corresponding to position 286 of SEQ ID NO: 1.

[Paragraph 37] The cellobiohydrolase variant of paragraph 36, wherein the substitution is with Ala.

[Paragraph 38] The cellobiohydrolase variant of any one of paragraphs 1-37, which comprises a substitution at a position corresponding to position 343 of SEQ ID NO: 1.

[Paragraph 39] The cellobiohydrolase variant of paragraph 38, wherein the substitution is with Glu or Gly.

[Paragraph 40] The cellobiohydrolase variant of any one of paragraphs 1-39, which comprises a substitution at two positions corresponding to any of positions 201, 243, 286, and 343 of SEQ ID NO: 1.

[Paragraph 41] The cellobiohydrolase variant of any one of paragraphs 1-39, which comprises a substitution at three positions corresponding to any of positions 201, 243, 286, and 343 of SEQ ID NO: 1.

[Paragraph 42] The cellobiohydrolase variant of any one of paragraphs 1-39, which comprises a substitution at each position corresponding to positions 201, 243, 286, and 343 of SEQ ID NO: 1.

[Paragraph 43] The cellobiohydrolase variant of any one of paragraphs 1-42, which comprises one or more substitutions selected from the group consisting of S201D, L243E, K,V, V286A, and S343E,G.

[Paragraph 44] The cellobiohydrolase variant of any one of paragraphs 1-43, which further comprises a substitution at one or more positions corresponding to positions 101, 143, 186, 217, 236, 245, 250, 251, 289, 295, 311, 321, 327, 333, 365, 374, 429, and 441 of SEQ ID NO: 1, e.g., E101H, S186Y, A236S, C245L, T251K, N289D, D321N, Q327K, L333F, G365E, G374C, T429Q, and N441C.

[Paragraph 45] The cellobiohydrolase variant of any one of paragraphs 1-44, which has an improved property relative to the parent, wherein the improved property is selected from the group consisting of improved glucose tolerance, catalytic efficiency, and catalytic rate.

[Paragraph 46] The cellobiohydrolase variant of any one of paragraphs 1-45 which has cellobiohydrolase II activity.

[Paragraph 47] An enzyme composition comprising a cellobiohydrolase variant of any one of paragraphs 1-46.

[Paragraph 48] The enzyme composition of paragraph 47, further comprising one or more enzymes selected from the group consisting of a cellulase, an AA9 polypeptide, a hemicellulase, a cellulose inducible protein, an esterase, an expansin, a ligninolytic enzyme, an oxidoreductase, a pectinase, a protease, and a swollenin.

[Paragraph 49] The enzyme composition of paragraph 48, wherein the cellulase is one or more enzymes selected from the group consisting of an endoglucanase, a cellobiohydrolase, and a beta-glucosidase.

[Paragraph 50] The enzyme composition of paragraph 48, wherein the hemicellulase is one or more enzymes selected from the group consisting of a xylanase, an acetylxylan esterase, a feruloyl esterase, an arabinofuranosidase, a xylosidase, and a glucuronidase.

[Paragraph 51] The enzyme composition of any one of paragraphs 47-50, further comprising a catalase.

[Paragraph 52] An isolated polynucleotide encoding the cellobiohydrolase variant of any one of paragraphs 1-46, which is operably linked to one or more control sequences that direct the production of the polypeptide in an expression host.

[Paragraph 53] A nucleic acid construct comprising the polynucleotide of paragraph 52.

[Paragraph 54] An expression vector comprising the polynucleotide of paragraph 52.

[Paragraph 55] A recombinant host cell comprising the polynucleotide of paragraph 52.

[Paragraph 56] A method of producing a cellobiohydrolase variant, comprising:
(a) cultivating the recombinant host cell of paragraph 55 under conditions conducive for production of the variant; and optionally
(b) recovering the variant.

[Paragraph 57] A transgenic plant, plant part or plant cell transformed with the polynucleotide of paragraph 52.

[Paragraph 58] A method of producing a cellobiohydrolase variant, comprising:
(a) cultivating a transgenic plant, plant part or a plant cell of paragraph 57 under conditions conducive for production of the variant; and optionally
(b) recovering the variant.

[Paragraph 59] A method for obtaining a cellobiohydrolase variant, comprising introducing into a parent cellobiohydrolase a substitution at one or more positions corresponding to positions 201, 243, 286, and 343 of the polypeptide of SEQ ID NO: 1, wherein the cellobiohydrolase variant has cellobiohydrolase activity; and recovering the variant.

[Paragraph 60] The method of paragraph 59, further comprising introducing into the parent cellobiohydrolase a substitution at one or more positions corresponding to positions 101, 143, 186, 217, 236, 245, 250, 251, 289, 295, 311, 321, 327, 333, 365, 374, 429, and 441 of SEQ ID NO: 1, e.g., E101H, S186Y, A236S, C245L, T251K, N289D, D321N, Q327K, L333F, G365E, G374C, T429Q, and N441C.

[Paragraph 61] A whole broth formulation or cell culture composition comprising the cellobiohydrolase variant of any one of paragraphs 1-46.

[Paragraph 62] A process for degrading a cellulosic material, comprising: treating the cellulosic material with an enzyme composition comprising the cellobiohydrolase variant of any one of paragraphs 1-46.

[Paragraph 63] The process of paragraph 62, wherein the cellulosic material is pretreated.

[Paragraph 64] The process of paragraph 62 or 63, wherein the enzyme composition further comprises one or more enzymes selected from the group consisting of a cellulase, an AA9 polypeptide, a hemicellulase, a cellulose inducible protein, an esterase, an expansin, a ligninolytic enzyme, an oxidoreductase, a pectinase, a protease, and a swollenin.

[Paragraph 65] The process of paragraph 64, wherein the cellulase is one or more enzymes selected from the group consisting of an endoglucanase, a cellobiohydrolase, and a beta-glucosidase.

[Paragraph 66] The process of paragraph 64, wherein the hemicellulase is one or more enzymes selected from the group consisting of a xylanase, an acetylxylan esterase, a feruloyl esterase, an arabinofuranosidase, a xylosidase, and a glucuronidase.

[Paragraph 67] The process of any one of paragraphs 62-66, further comprising recovering the degraded cellulosic material.

[Paragraph 68] The process of paragraph 67, wherein the degraded cellulosic material is a sugar.

[Paragraph 69] The process of paragraph 68, wherein the sugar is selected from the group consisting of glucose, xylose, mannose, galactose, and arabinose.

[Paragraph 70] A process for producing a fermentation product, comprising:
(a) saccharifying a cellulosic material with an enzyme composition comprising a cellobiohydrolase variant of any one of paragraphs 1-46;
(b) fermenting the saccharified cellulosic material with one or more fermenting microorganisms to produce the fermentation product; and
(c) recovering the fermentation product from the fermentation.

[Paragraph 71] The process of paragraph 70, wherein the cellulosic material is pretreated.

[Paragraph 72] The process of paragraph 70 or 71, wherein the enzyme composition further comprises one or more enzymes selected from the group consisting of a cellulase, an AA9 polypeptide, a hemicellulase, a cellulose inducible protein, an esterase, an expansin, a ligninolytic enzyme, an oxidoreductase, a pectinase, a protease, and a swollenin.

[Paragraph 73] The process of paragraph 72, wherein the cellulase is one or more enzymes selected from the group consisting of an endoglucanase, a cellobiohydrolase, and a beta-glucosidase.

[Paragraph 74] The process of paragraph 72, wherein the hemicellulase is one or more enzymes selected from the group consisting of a xylanase, an acetylxylan esterase, a feruloyl esterase, an arabinofuranosidase, a xylosidase, and a glucuronidase.

[Paragraph 75] The process of any one of paragraphs 70-74, wherein steps (a) and (b) are performed simultaneously in a simultaneous saccharification and fermentation.

[Paragraph 76] The process of any one of paragraphs 70-75, wherein the fermentation product is an alcohol, an alkane, a cycloalkane, an alkene, an amino acid, a gas, isoprene, a ketone, an organic acid, or polyketide.

[Paragraph 77] A process of fermenting a cellulosic material, comprising: fermenting the cellulosic material with one or more fermenting microorganisms, wherein the cellulosic material is saccharified with an enzyme composition comprising a cellobiohydrolase variant of any one of paragraphs 1-46.

[Paragraph 78] The process of paragraph 77, wherein the fermenting of the cellulosic material produces a fermentation product.

[Paragraph 79] The process of paragraph 78, further comprising recovering the fermentation product from the fermentation.

[Paragraph 80] The process of paragraph 78 or 79, wherein the fermentation product is an alcohol, an alkane, a cycloalkane, an alkene, an amino acid, a gas, isoprene, a ketone, an organic acid, or polyketide.

[Paragraph 81] The process of any one of paragraphs 77-80, wherein the cellulosic material is pretreated before saccharification.

[Paragraph 82] The process of any one of paragraphs 77-81, wherein the enzyme composition further comprises one or more enzymes selected from the group consisting of a cellulase, an AA9 polypeptide, a hemicellulase, a cellulose inducible protein, an esterase, an expansin, a ligninolytic enzyme, an oxidoreductase, a pectinase, a protease, and a swollenin.

[Paragraph 83] The process of paragraph 82, wherein the cellulase is one or more enzymes selected from the group consisting of an endoglucanase, a cellobiohydrolase, and a beta-glucosidase.

[Paragraph 84] The process of paragraph 82, wherein the hemicellulase is one or more enzymes selected from the group consisting of a xylanase, an acetylxylan esterase, a feruloyl esterase, an arabinofuranosidase, a xylosidase, and a glucuronidase.

[Paragraph 85] The process of any one of paragraphs 62-84, wherein oxygen is added during saccharification to maintain a concentration of dissolved oxygen in the range of at least 0.5-10% of the saturation level.

[Paragraph 86] The method of paragraph 85, wherein the dissolved oxygen concentration during saccharification is in the range of 0.5-10% of the saturation level, such as 0.5-7%, such as 0.5-5%, such as 0.5-4%, such as 0.5-3%, such as 0.5-2%, such as 1-5%, such as 1-4%, such as 1-3%, such as 1-2%.

[Paragraph 87] The process of any one of paragraphs 62-86, wherein the enzyme composition further comprises a catalase.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A cellobiohydrolase variant, comprising a substitution at one or more positions corresponding to positions 201, 243, 286, and 343 of the polypeptide of SEQ ID NO: 1, wherein the variant has cellobiohydrolase activity, wherein the substitution at a position corresponding to position 201 is with Asp, the substitution at a position corresponding to position 243 is with Glu, Lys, or Val, the substitution at a position corresponding to position 286 is with Ala, and the substitution at a position corresponding to position 343 is with Glu or Gly, and wherein the variant has at least 85% sequence identity, but less than 100% sequence identity, to the cellobiohydrolase of SEQ ID NO: 1, 2, 4, 5, 6, 7, 8, or 9, or at least 95% sequence identity, but less than 100% sequence identity, to the cellobiohydrolase of SEQ ID NO: 3.

2. The cellobiohydrolase variant of claim 1, which has at least 90% sequence identity, but less than 100% sequence identity, to the cellobiohydrolase of SEQ ID NO: 1, 2, 4, 5, 6, 7, 8, or 9.

3. A cellobiohydrolase variant, comprising a variant catalytic domain, wherein the variant catalytic domain comprises a substitution at one or more positions corresponding to positions 201, 243, 286, and 343 of SEQ ID NO: 1, wherein the substitution at a position corresponding to position 201 is with Asp, the substitution at a position corresponding to position 243 is with Glu, Lys, or Val, the substitution at a position corresponding to position 286 is with Ala, and the substitution at a position corresponding to position 343 is with Glu or Gly, and wherein the variant catalytic domain has at least 85% sequence identity, but less than 100% sequence identity, to the catalytic domain of the cellobiohydrolase of SEQ ID NO: 1, 2, 4, 5, 6, 7, 8, or 9, or at least 95% sequence identity, but less than 100% sequence identity, to the catalytic domain of the cellobiohydrolase of SEQ ID NO: 3.

4. The cellobiohydrolase variant of claim 3, wherein the catalytic domain of the cellobiohydrolase has at least 90% sequence identity, but less than 100% sequence identity, to the catalytic domain of the cellobiohydrolase of SEQ ID NO: 1, 2, 4, 5, 6, 7, 8, or 9.

5. The cellobiohydrolase variant of claim 3, which further comprises a carbohydrate binding module.

6. The cellobiohydrolase variant of claim 1, which comprises one or more substitutions selected from the group consisting of S201D, L243E,K,V, V286A, and S343E,G of SEQ ID NO: 1.

7. The cellobiohydrolase variant of claim 1, which further comprises a substitution at one or more positions corresponding to positions 101, 143, 186, 217, 236, 245, 250, 251, 289, 295, 311, 321, 327, 333, 365, 374, 429, and 441 of SEQ ID NO: 1, wherein the substitution at a position corresponding to position 101 is with His, the substitution at a position corresponding to position 186 is with Tyr, the substitution at a position corresponding to position 236 is with Ser, the substitution at a position corresponding to position 245 is with Lys, the substitution at a position corresponding to position 251 is with Lys, the substitution at a position corresponding to position 289 is with Asp, the substitution at a position corresponding to position 321 is with Asn, the substitution at a position corresponding to position 327 is with Lys, the substitution at a position corresponding to position 333 is with Phe, the substitution at a position corresponding to position 365 is with Glu, the substitution at a position corresponding to position 374 is with Cys, the substitution at a position corresponding to position 429 is with Gln, and the substitution at a position corresponding to position 441 is with Cys.

8. The cellobiohydrolase variant of claim 1, wherein the variant has an improved property relative to a cellobiohydrolase without the substitution at one or more positions corresponding to positions 201, 243, 286, and 343, wherein the improved property is selected from the group consisting of improved glucose tolerance, catalytic efficiency, and catalytic rate.

9. An enzyme composition, whole broth formulation or cell culture composition comprising the cellobiohydrolase variant of claim 1.

10. A method for obtaining the cellobiohydrolase variant of claim 1, comprising introducing into a parent cellobiohydrolase a substitution at one or more positions corresponding to positions 201, 243, 286, and 343 of the polypeptide of SEQ ID NO: 1, wherein the cellobiohydrolase variant has cellobiohydrolase activity, wherein the substitution at a position corresponding to position 201 is with Asp, the substitution at a position corresponding to position 243 is with Glu, Lys, or Val, the substitution at a position corresponding to position 286 is with Ala, and the substitution at a position corresponding to position 343 is with Glu or Gly, and wherein the variant has at least 85% sequence identity, but less than 100% sequence identity, to the cellobiohydrolase of SEQ ID NO: 1, 2, 4, 5, 6, 7, 8, or 9, or at least 95% sequence identity, but less than 100% sequence identity, to the cellobiohydrolase of SEQ ID NO: 3; and recovering the variant.

11. A process for degrading a cellulosic material, comprising: treating the cellulosic material with an enzyme composition comprising the cellobiohydrolase variant of claim 1, and optionally recovering the degraded cellulosic material.

12. A process for producing a fermentation product, comprising:
(a) saccharifying a cellulosic material with an enzyme composition comprising a cellobiohydrolase variant of claim 1;
(b) fermenting the saccharified cellulosic material with one or more fermenting microorganisms to produce the fermentation product; and
(c) recovering the fermentation product from the fermentation.

13. A process of fermenting a cellulosic material, comprising: fermenting the cellulosic material with one or more fermenting microorganisms, wherein the cellulosic material is saccharified with an enzyme composition comprising a cellobiohydrolase variant of claim 1, and wherein the fermenting of the cellulosic material produces a fermentation product.

14. The cellobiohydrolase variant of claim 1, which has at least 95% sequence identity, but less than 100% sequence identity, to the cellobiohydrolase of SEQ ID NO: 1, 2, 3, 4, 5, 6, 7, 8, or 9.

15. The cellobiohydrolase variant of claim 3, wherein the catalytic domain of the cellobiohydrolase has at least 95% sequence identity, but less than 100% sequence identity, to the catalytic domain of the cellobiohydrolase of SEQ ID NO: 1, 2, 3, 4, 5, 6, 7, 8, or 9.

16. The cellobiohydrolase variant of claim 5, wherein the carbohydrate binding module is heterologous to the catalytic domain.

17. The cellobiohydrolase variant of claim 7, which comprises one or more substitutions selected from the group consisting of E101H, S186Y, A236S, C245L, T251K, N289D, D321N, Q327K, L333F, G365E, G374C, T429Q, and N441C of SEQ ID NO: 1.

* * * * *

SEQUENCE LISTING

```
<160> NUMBER OF SEQ ID NOS: 37

<210> SEQ ID NO 1
<211> LENGTH: 446
<212> TYPE: PRT
<213> ORGANISM: Talaromyces leycettanus

<400> SEQUENCE: 1

Gln Gln Thr Met Trp Gly Gln Cys Gly Gly Gln Gly Trp Thr Gly Pro
1               5                   10                  15

Thr Ile Cys Val Ala Gly Ala Thr Cys Ser Thr Gln Asn Pro Trp Tyr
            20                  25                  30

Ala Gln Cys Thr Pro Ala Pro Thr Ala Pro Thr Thr Leu Gln Thr Thr
        35                  40                  45

Thr Thr Thr Ser Ser Lys Ser Ser Thr Thr Thr Ser Ser Lys Ser Ser
    50                  55                  60

Thr Thr Thr Gly Gly Ser Gly Gly Gly Thr Thr Thr Ser Thr Ser Ala
65                  70                  75                  80

Thr Ile Thr Ala Ala Pro Ser Gly Asn Pro Tyr Ser Gly Tyr Gln Leu
                85                  90                  95

Tyr Val Asn Gln Glu Tyr Ser Ser Glu Val Tyr Ala Ser Ala Ile Pro
            100                 105                 110

Ser Leu Thr Gly Thr Leu Val Ala Lys Ala Ser Ala Ala Ala Glu Val
        115                 120                 125

Pro Ser Phe Leu Trp Leu Asp Thr Ala Ser Lys Val Pro Leu Met Gly
    130                 135                 140

Thr Tyr Leu Gln Asp Ile Gln Ala Lys Asn Ala Ala Gly Ala Asn Pro
145                 150                 155                 160

Pro Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asn Asn Gly Val
            180                 185                 190

Ala Asn Tyr Lys Ala Tyr Ile Asp Ser Ile Arg Ala Leu Leu Val Gln
        195                 200                 205

Tyr Ser Asn Val His Val Ile Leu Val Ile Glu Pro Asp Ser Leu Ala
    210                 215                 220

Asn Leu Val Thr Asn Leu Asn Val Gln Lys Cys Ala Asn Ala Gln Ser
225                 230                 235                 240

Ala Tyr Leu Glu Cys Ile Asn Tyr Ala Leu Thr Gln Leu Asn Leu Lys
                245                 250                 255

Asn Val Ala Met Tyr Ile Asp Ala Gly His Ala Gly Trp Leu Gly Trp
            260                 265                 270

Pro Ala Asn Leu Ser Pro Ala Ala Gln Leu Phe Ala Ser Val Tyr Gln
        275                 280                 285
```

```
Asn Ala Ser Ser Pro Ala Ala Val Arg Gly Leu Ala Thr Asn Val Ala
    290                 295                 300

Asn Tyr Asn Ala Trp Ser Ile Ala Thr Cys Pro Ser Tyr Thr Gln Gly
305                 310                 315                 320

Asp Pro Asn Cys Asp Glu Gln Lys Tyr Ile Asn Ala Leu Ala Pro Leu
                325                 330                 335

Leu Gln Gln Gln Gly Trp Ser Val His Phe Ile Thr Asp Thr Gly
                340                 345                 350

Arg Asn Gly Val Gln Pro Thr Lys Gln Asn Ala Trp Gly Asp Trp Cys
                355                 360                 365

Asn Val Ile Gly Thr Gly Phe Gly Val Arg Pro Thr Thr Asn Thr Gly
    370                 375                 380

Asp Pro Leu Glu Asp Ala Phe Val Trp Val Lys Pro Gly Gly Glu Ser
385                 390                 395                 400

Asp Gly Thr Ser Asn Ser Thr Ser Pro Arg Tyr Asp Ala His Cys Gly
                405                 410                 415

Tyr Ser Asp Ala Leu Gln Pro Ala Pro Glu Ala Gly Thr Trp Phe Glu
                420                 425                 430

Ala Tyr Phe Glu Gln Leu Leu Thr Asn Ala Asn Pro Ser Phe
    435                 440                 445

<210> SEQ ID NO 2
<211> LENGTH: 453
<212> TYPE: PRT
<213> ORGANISM: Trichoderma reesei

<400> SEQUENCE: 2

Val Pro Leu Glu Glu Arg Gln Ala Cys Ser Ser Val Trp Gly Gln Cys
1               5                   10                  15

Gly Gly Gln Asn Trp Ser Gly Pro Thr Cys Cys Ala Ser Gly Ser Thr
                20                  25                  30

Cys Val Tyr Ser Asn Asp Tyr Tyr Ser Gln Cys Leu Pro Gly Ala Ala
            35                  40                  45

Ser Ser Ser Ser Ser Thr Arg Ala Ala Ser Thr Thr Ser Arg Val Ser
    50                  55                  60

Pro Thr Thr Ser Arg Ser Ser Ser Ala Thr Pro Pro Gly Ser Thr
65                  70                  75                  80

Thr Thr Arg Val Pro Pro Val Gly Ser Gly Thr Ala Thr Tyr Ser Gly
                85                  90                  95

Asn Pro Phe Val Gly Val Thr Pro Trp Ala Asn Ala Tyr Tyr Ala Ser
                100                 105                 110

Glu Val Ser Ser Leu Ala Ile Pro Ser Leu Thr Gly Ala Met Ala Thr
            115                 120                 125

Ala Ala Ala Ala Val Ala Lys Val Pro Ser Phe Met Trp Leu Asp Thr
    130                 135                 140

Leu Asp Lys Thr Pro Leu Met Glu Gln Thr Leu Ala Asp Ile Arg Thr
145                 150                 155                 160

Ala Asn Lys Asn Gly Gly Asn Tyr Ala Gly Gln Phe Val Val Tyr Asp
                165                 170                 175

Leu Pro Asp Arg Asp Cys Ala Ala Leu Ala Ser Asn Gly Glu Tyr Ser
                180                 185                 190

Ile Ala Asp Gly Gly Val Ala Lys Tyr Lys Asn Tyr Ile Asp Thr Ile
        195                 200                 205

Arg Gln Ile Val Val Glu Tyr Ser Asp Ile Arg Thr Leu Leu Val Ile
    210                 215                 220
```

Glu Pro Asp Ser Leu Ala Asn Leu Val Thr Asn Leu Gly Thr Pro Lys
225                 230                 235                 240

Cys Ala Asn Ala Gln Ser Ala Tyr Leu Glu Cys Ile Asn Tyr Ala Val
                245                 250                 255

Thr Gln Leu Asn Leu Pro Asn Val Ala Met Tyr Leu Asp Ala Gly His
                260                 265                 270

Ala Gly Trp Leu Gly Trp Pro Ala Asn Gln Asp Pro Ala Ala Gln Leu
            275                 280                 285

Phe Ala Asn Val Tyr Lys Asn Ala Ser Ser Pro Arg Ala Leu Arg Gly
290                 295                 300

Leu Ala Thr Asn Val Ala Asn Tyr Asn Gly Trp Asn Ile Thr Ser Pro
305                 310                 315                 320

Pro Ser Tyr Thr Gln Gly Asn Ala Val Tyr Asn Glu Lys Leu Tyr Ile
                325                 330                 335

His Ala Ile Gly Pro Leu Leu Ala Asn His Gly Trp Ser Asn Ala Phe
                340                 345                 350

Phe Ile Thr Asp Gln Gly Arg Ser Gly Lys Gln Pro Thr Gly Gln Gln
                355                 360                 365

Gln Trp Gly Asp Trp Cys Asn Val Ile Gly Thr Gly Phe Gly Ile Arg
            370                 375                 380

Pro Ser Ala Asn Thr Gly Asp Ser Leu Leu Asp Ser Phe Val Trp Val
385                 390                 395                 400

Lys Pro Gly Gly Glu Cys Asp Gly Thr Ser Asp Ser Ser Ala Pro Arg
                405                 410                 415

Phe Asp Ser His Cys Ala Leu Pro Asp Ala Leu Gln Pro Ala Pro Gln
                420                 425                 430

Ala Gly Ala Trp Phe Gln Ala Tyr Phe Val Gln Leu Leu Thr Asn Ala
            435                 440                 445

Asn Pro Ser Phe Leu
    450

<210> SEQ ID NO 3
<211> LENGTH: 450
<212> TYPE: PRT
<213> ORGANISM: Fusarium solani

<400> SEQUENCE: 3

Ala Pro Leu Val Glu Glu Arg Gln Ala Cys Ala Ala Gln Trp Ala Gln
1               5                   10                  15

Cys Gly Gly Phe Ser Trp Asn Gly Ala Thr Cys Cys Gln Ser Gly Ser
                20                  25                  30

Tyr Cys Ser Lys Ile Asn Asp Tyr Tyr Ser Gln Cys Ile Pro Gly Glu
            35                  40                  45

Gly Pro Ala Thr Ser Lys Ser Ser Thr Leu Pro Ala Ser Thr Thr Thr
    50                  55                  60

Thr Gln Pro Thr Ser Thr Ser Thr Ala Gly Thr Ser Thr Ser Thr Lys
65                  70                  75                  80

Pro Pro Pro Ala Gly Ser Gly Thr Ala Thr Tyr Ser Gly Asn Pro Tyr
                85                  90                  95

Ser Gly Val Asn Leu Trp Ala Asn Ser Tyr Tyr Arg Ser Glu Val Thr
            100                 105                 110

Asn Leu Ala Ile Pro Lys Leu Ser Gly Ala Met Ala Thr Ala Ala Ala
        115                 120                 125

Lys Val Ala Asp Val Pro Ser Tyr Gln Trp Met Asp Ser Phe Asp His

```
                130                 135                 140
Ile Ser Leu Met Glu Asp Thr Leu Val Asp Ile Arg Lys Ala Asn Leu
145                 150                 155                 160

Ala Gly Gly Asn Tyr Ala Gly Gln Phe Val Val Tyr Asp Leu Pro Asp
                165                 170                 175

Arg Asp Cys Ala Ala Ala Ser Asn Gly Glu Tyr Ser Leu Asp Asn
                180                 185                 190

Asp Gly Ala Asn Lys Tyr Lys Asn Tyr Ile Gln Thr Ile Lys Lys Ile
                195                 200                 205

Ile Gln Ser Tyr Ser Asp Ile Arg Ile Leu Leu Val Ile Glu Pro Asp
210                 215                 220

Ser Leu Ala Asn Leu Val Thr Asn Met Asp Val Ala Lys Cys Ala Lys
225                 230                 235                 240

Ala His Asp Ala Tyr Ile Ser Leu Thr Asn Tyr Ala Val Thr Glu Leu
                245                 250                 255

Asn Leu Pro Asn Val Ala Met Tyr Leu Asp Ala Gly His Ala Gly Trp
                260                 265                 270

Leu Gly Trp Pro Ala Asn Gln Gly Pro Ala Ala Lys Leu Phe Ala Ser
                275                 280                 285

Ile Tyr Lys Asp Ala Gly Lys Pro Ala Ala Leu Arg Gly Leu Ala Thr
290                 295                 300

Asn Val Ala Asn Tyr Asn Ala Trp Ser Leu Ser Ser Ala Pro Pro Tyr
305                 310                 315                 320

Thr Gln Gly Ala Ser Ile Tyr Asp Glu Lys Ser Phe Ile His Ala Met
                325                 330                 335

Gly Pro Leu Leu Glu Gln Asn Gly Trp Pro Gly Ala His Phe Ile Thr
                340                 345                 350

Asp Gln Gly Arg Ser Gly Lys Gln Pro Thr Gly Gln Ile Gln Trp Gly
                355                 360                 365

Asp Trp Cys Asn Ser Lys Gly Thr Gly Phe Gly Ile Arg Pro Ser Ala
                370                 375                 380

Asn Thr Gly Asp Ser Leu Leu Asp Ala Phe Val Trp Val Lys Pro Gly
385                 390                 395                 400

Gly Glu Ser Asp Gly Thr Ser Asp Thr Ser Ala Thr Arg Tyr Asp Tyr
                405                 410                 415

His Cys Gly Ala Ser Ala Ala Leu Gln Pro Ala Pro Glu Ala Gly Thr
                420                 425                 430

Trp Phe Gln Ala Tyr Phe Glu Gln Leu Leu Thr Asn Ala Asn Pro Ser
                435                 440                 445

Phe Leu
450

<210> SEQ ID NO 4
<211> LENGTH: 465
<212> TYPE: PRT
<213> ORGANISM: Myceliophthora thermophila

<400> SEQUENCE: 4

Ala Pro Val Ile Glu Glu Arg Gln Asn Cys Gly Ala Val Trp Thr Gln
1               5                   10                  15

Cys Gly Gly Asn Gly Trp Gln Gly Pro Thr Cys Cys Ala Ser Gly Ser
                20                  25                  30

Thr Cys Val Ala Gln Asn Glu Trp Tyr Ser Gln Cys Leu Pro Asn Ser
                35                  40                  45
```

```
Gln Val Thr Ser Ser Thr Thr Pro Ser Ser Thr Ser Thr Ser Gln Arg
    50              55                  60

Ser Thr Ser Thr Ser Ser Ser Thr Thr Arg Ser Gly Ser Ser Ser Ser
65              70              75                  80

Ser Ser Thr Thr Pro Pro Pro Val Ser Ser Pro Val Thr Ser Ile Pro
                85              90              95

Gly Gly Ala Thr Ser Thr Ala Ser Tyr Ser Gly Asn Pro Phe Ser Gly
            100             105             110

Val Arg Leu Phe Ala Asn Asp Tyr Tyr Arg Ser Glu Val His Asn Leu
        115             120             125

Ala Ile Pro Ser Met Thr Gly Thr Leu Ala Ala Lys Ala Ser Ala Val
    130             135             140

Ala Glu Val Pro Ser Phe Gln Trp Leu Asp Arg Asn Val Thr Ile Asp
145             150             155             160

Thr Leu Met Val Gln Thr Leu Ser Gln Val Arg Ala Leu Asn Lys Ala
            165             170             175

Gly Ala Asn Pro Pro Tyr Ala Ala Gln Leu Val Val Tyr Asp Leu Pro
            180             185             190

Asp Arg Asp Cys Ala Ala Ala Ser Asn Gly Glu Phe Ser Ile Ala
        195             200             205

Asn Gly Gly Ala Ala Asn Tyr Arg Ser Tyr Ile Asp Ala Ile Arg Lys
        210             215             220

His Ile Ile Glu Tyr Ser Asp Ile Arg Ile Ile Leu Val Ile Glu Pro
225             230             235             240

Asp Ser Met Ala Asn Met Val Thr Asn Met Asn Val Ala Lys Cys Ser
            245             250             255

Asn Ala Ala Ser Thr Tyr His Glu Leu Thr Val Tyr Ala Leu Lys Gln
            260             265             270

Leu Asn Leu Pro Asn Val Ala Met Tyr Leu Asp Ala Gly His Ala Gly
        275             280             285

Trp Leu Gly Trp Pro Ala Asn Ile Gln Pro Ala Ala Glu Leu Phe Ala
        290             295             300

Gly Ile Tyr Asn Asp Ala Gly Lys Pro Ala Ala Val Arg Gly Leu Ala
305             310             315             320

Thr Asn Val Ala Asn Tyr Asn Ala Trp Ser Ile Ala Ser Ala Pro Ser
            325             330             335

Tyr Thr Ser Pro Asn Pro Asn Tyr Asp Glu Lys His Tyr Ile Glu Ala
            340             345             350

Phe Ser Pro Leu Leu Asn Ser Ala Gly Phe Pro Ala Arg Phe Ile Val
        355             360             365

Asp Thr Gly Arg Asn Gly Lys Gln Pro Thr Gly Gln Gln Gln Trp Gly
    370             375             380

Asp Trp Cys Asn Val Lys Gly Thr Gly Phe Gly Val Arg Pro Thr Ala
385             390             395             400

Asn Thr Gly His Glu Leu Val Asp Ala Phe Val Trp Val Lys Pro Gly
            405             410             415

Gly Glu Ser Asp Gly Thr Ser Asp Thr Ser Ala Ala Arg Tyr Asp Tyr
            420             425             430

His Cys Gly Leu Ser Asp Ala Leu Gln Pro Ala Pro Glu Ala Gly Gln
        435             440             445

Trp Phe Gln Ala Tyr Phe Glu Gln Leu Leu Thr Asn Ala Asn Pro Pro
450             455             460

Phe
```

<210> SEQ ID NO 5
<211> LENGTH: 451
<212> TYPE: PRT
<213> ORGANISM: Artificial sequence
<220> FEATURE:
<223> OTHER INFORMATION: Synthetic construct

<400> SEQUENCE: 5

```
Gln Asn Cys Gln Thr Val Trp Gly Gln Cys Gly Gly Gln Gly Trp Thr
1               5                   10                  15
Gly Ala Thr Ser Cys Val Ala Gly Ala Thr Cys Ser Thr Leu Asn Pro
            20                  25                  30
Tyr Tyr Ala Gln Cys Leu Pro Ala Thr Ala Thr Thr Thr Thr Thr Thr
        35                  40                  45
Thr Thr Pro Thr Thr Thr Ser Ser Thr Thr Thr Thr Ser Thr Thr
50                  55                  60
Thr Thr Ser Thr Thr Thr Thr Pro Thr Thr Thr Thr Thr Thr Thr Ser
65                  70                  75                  80
Ala Pro Ser Gly Pro Thr Thr Ala Thr Ala Ser Gly Pro Phe Ser
                85                  90                  95
Gly Tyr Gln Leu Tyr Ala Asn Pro Tyr Tyr Ser Ser Glu Val His Thr
            100                 105                 110
Leu Ala Ile Pro Ser Leu Thr Asp Gly Ser Leu Ala Pro Lys Ala Ser
        115                 120                 125
Ala Val Ala Lys Val Pro Ser Phe Val Trp Leu Asp Thr Ala Ala Lys
130                 135                 140
Val Pro Thr Met Gly Thr Tyr Leu Ala Asp Ile Gln Ala Lys Asn Lys
145                 150                 155                 160
Ala Gly Ala Asn Pro Pro Ile Ala Gly Ile Phe Val Val Tyr Asp Leu
                165                 170                 175
Pro Asp Arg Asp Cys Ala Ala Leu Ala Ser Asn Gly Glu Tyr Ser Ile
            180                 185                 190
Ala Asn Asn Gly Val Ala Asn Tyr Lys Ala Tyr Ile Asp Ser Ile Arg
        195                 200                 205
Ala Gln Leu Lys Lys Tyr Ser Asp Val His Thr Ile Leu Val Ile Glu
210                 215                 220
Pro Asp Ser Leu Ala Asn Leu Val Thr Asn Leu Asn Val Ala Lys Cys
225                 230                 235                 240
Ala Asn Ala Gln Ser Ala Tyr Leu Glu Cys Val Asn Tyr Ala Leu Thr
                245                 250                 255
Gln Leu Asn Leu Pro Asn Val Ala Met Tyr Leu Asp Ala Gly His Ala
            260                 265                 270
Gly Trp Leu Gly Trp Pro Ala Asn Leu Gly Pro Ala Ala Gln Leu Phe
        275                 280                 285
Ala Ser Val Tyr Lys Asn Ala Gly Ser Pro Ala Ala Val Arg Gly Leu
290                 295                 300
Ala Thr Asn Val Ala Asn Tyr Asn Ala Trp Ser Ile Ser Ser Cys Pro
305                 310                 315                 320
Ser Tyr Thr Gln Gly Asp Ser Asn Cys Asp Glu Lys Arg Tyr Ile Asn
                325                 330                 335
Ala Leu Ala Pro Leu Leu Lys Ala Gln Gly Phe Ser Asp Ala His Phe
            340                 345                 350
Ile Met Asp Thr Ser Arg Asn Gly Val Gln Pro Thr Lys Gln Gln Ala
```

```
            355                 360                 365
Trp Gly Asp Trp Cys Asn Val Ile Gly Thr Gly Phe Gly Val Arg Pro
        370                 375                 380

Thr Thr Asn Thr Gly Asp Pro Leu Glu Asp Ala Phe Val Trp Val Lys
385                 390                 395                 400

Pro Gly Gly Glu Ser Asp Gly Thr Ser Asp Thr Ser Ala Ala Arg Tyr
                405                 410                 415

Asp Ala His Cys Gly Tyr Ser Asp Ala Leu Gln Pro Ala Pro Glu Ala
            420                 425                 430

Gly Thr Trp Phe Gln Ala Tyr Phe Glu Gln Leu Leu Thr Asn Ala Asn
        435                 440                 445

Pro Ser Phe
    450

<210> SEQ ID NO 6
<211> LENGTH: 451
<212> TYPE: PRT
<213> ORGANISM: Artificial sequence
<220> FEATURE:
<223> OTHER INFORMATION: Synthetic construct

<400> SEQUENCE: 6

Gln Asn Cys Gln Thr Val Trp Gly Gln Cys Gly Gly Gln Gly Trp Thr
1               5                   10                  15

Gly Ala Thr Ser Cys Val Ala Gly Ala Ala Cys Ser Thr Leu Asn Pro
            20                  25                  30

Tyr Tyr Ala Gln Cys Leu Pro Ala Thr Ala Thr Thr Thr Thr Thr Thr
        35                  40                  45

Thr Thr Thr Thr Thr Thr Thr Ser Ser Thr Thr Thr Thr Ser Thr Thr
    50                  55                  60

Thr Ser Ser Thr Thr Thr Thr Pro Thr Thr Thr Thr Thr Thr Thr Thr
65                  70                  75                  80

Ala Pro Ser Ser Val Thr Thr Thr Ala Thr Ala Ser Gly Pro Phe Ser
                85                  90                  95

Gly Tyr Gln Leu Tyr Ala Asn Pro Tyr Tyr Ser Ser Glu Val His Thr
            100                 105                 110

Leu Ala Ile Pro Ser Leu Thr Asp Gly Ser Leu Ala Pro Lys Ala Ser
        115                 120                 125

Ala Val Ala Lys Val Pro Ser Phe Val Trp Leu Asp Thr Ala Ala Lys
    130                 135                 140

Val Pro Thr Met Gly Thr Tyr Leu Ala Asp Ile Arg Ala Lys Asn Ala
145                 150                 155                 160

Ala Gly Ala Asn Pro Pro Ile Ala Gly Ile Phe Val Val Tyr Asp Leu
                165                 170                 175

Pro Asp Arg Asp Cys Ala Ala Leu Ala Ser Asn Gly Glu Tyr Ser Ile
            180                 185                 190

Ala Asn Asn Gly Val Ala Asn Tyr Lys Ala Tyr Ile Asp Ser Ile Arg
        195                 200                 205

Ala Gln Leu Val Lys Tyr Ser Asp Val His Thr Ile Leu Val Ile Glu
    210                 215                 220

Pro Asp Ser Leu Ala Asn Leu Val Thr Asn Leu Asn Val Ala Lys Cys
225                 230                 235                 240

Ala Asn Ala Gln Ser Ala Tyr Leu Glu Cys Ile Asn Tyr Ala Leu Thr
                245                 250                 255

Gln Leu Asn Leu Pro Asn Val Ala Met Tyr Leu Asp Ala Gly His Ala
```

```
                260                 265                 270
Gly Trp Leu Gly Trp Pro Ala Asn Leu Ser Pro Ala Ala Gln Leu Phe
            275                 280                 285
Ala Ser Val Tyr Lys Asn Ala Gly Ser Pro Ala Ala Leu Arg Gly Leu
        290                 295                 300
Ala Thr Asn Val Ala Asn Tyr Asn Ala Trp Ser Ile Ser Thr Cys Pro
305                 310                 315                 320
Ser Tyr Thr Gln Gly Asp Ser Asn Cys Asp Glu Lys Arg Tyr Ile Asn
                325                 330                 335
Ala Leu Ala Pro Leu Leu Lys Ala Gln Gly Phe Pro Asp Ala His Phe
            340                 345                 350
Ile Met Asp Thr Ser Arg Asn Gly Val Gln Pro Thr Lys Gln Gln Ala
        355                 360                 365
Trp Gly Asp Trp Cys Asn Val Ile Gly Thr Gly Phe Gly Val Arg Pro
    370                 375                 380
Thr Thr Asn Thr Gly Asp Pro Leu Gln Asp Ala Phe Val Trp Val Lys
385                 390                 395                 400
Pro Gly Gly Glu Ser Asp Gly Thr Ser Asp Thr Ser Ala Ala Arg Tyr
                405                 410                 415
Asp Ala His Cys Gly Tyr Ser Asp Ala Leu Gln Pro Ala Pro Glu Ala
            420                 425                 430
Gly Thr Trp Phe Gln Ala Tyr Phe Glu Gln Leu Leu Thr Asn Ala Asn
        435                 440                 445
Pro Ser Phe
    450

<210> SEQ ID NO 7
<211> LENGTH: 451
<212> TYPE: PRT
<213> ORGANISM: Artificial sequence
<220> FEATURE:
<223> OTHER INFORMATION: Synthetic construct

<400> SEQUENCE: 7

Gln Ala Cys Gln Thr Val Trp Gly Gln Cys Gly Gly Gln Gly Trp Thr
1               5                   10                  15
Gly Ala Thr Ser Cys Val Ala Gly Ala Ala Cys Ser Thr Leu Asn Pro
            20                  25                  30
Tyr Tyr Ala Gln Cys Leu Pro Ala Thr Ala Thr Thr Thr Thr Thr Thr
        35                  40                  45
Thr Thr Thr Thr Thr Thr Ser Ser Thr Thr Thr Thr Ser Thr Thr Thr
    50                  55                  60
Thr Ser Ser Thr Thr Thr Thr Pro Thr Thr Thr Thr Thr Thr Thr Ser
65                  70                  75                  80
Ala Pro Ser Gly Val Thr Thr Ala Thr Ala Ser Gly Pro Phe Ser
            85                  90                  95
Gly Tyr Gln Leu Tyr Ala Asn Pro Tyr Tyr Ser Ser Glu Val His Thr
        100                 105                 110
Leu Ala Ile Pro Ser Leu Thr Asp Gly Ser Leu Ala Pro Lys Ala Thr
    115                 120                 125
Ala Val Ala Lys Val Pro Ser Phe Val Trp Leu Asp Thr Ala Ala Lys
130                 135                 140
Val Pro Thr Met Gly Thr Tyr Leu Ala Asp Ile Arg Ala Gln Asn Ala
            150                 155                 160
Ala Gly Ala Asn Pro Pro Ile Ala Gly Ile Phe Val Val Tyr Asp Leu
```

```
                165                 170                 175
Pro Asp Arg Asp Cys Ala Ala Leu Ala Ser Asn Gly Glu Tyr Ser Ile
            180                 185                 190

Ala Asn Asn Gly Val Ala Asn Tyr Lys Ala Tyr Ile Asp Ser Ile Arg
            195                 200                 205

Ala Gln Leu Val Lys Tyr Ser Asp Val His Thr Ile Leu Val Ile Glu
            210                 215                 220

Pro Asp Ser Leu Ala Asn Leu Val Thr Asn Leu Asn Val Ala Lys Cys
225                 230                 235                 240

Ala Asn Ala Gln Ser Ala Tyr Leu Glu Cys Ile Asn Tyr Ala Leu Thr
                245                 250                 255

Gln Leu Asn Leu Pro Asn Val Ala Met Tyr Leu Asp Ala Gly His Ala
            260                 265                 270

Gly Trp Leu Gly Trp Pro Ala Asn Leu Ser Pro Ala Ala Gln Leu Phe
            275                 280                 285

Ala Ser Val Tyr Lys Asn Ala Gly Ser Pro Ala Ala Leu Arg Gly Leu
            290                 295                 300

Ala Thr Asn Val Ala Asn Tyr Asn Ala Trp Ser Ile Ser Thr Cys Pro
305                 310                 315                 320

Ser Tyr Thr Gln Gly Asp Ser Asn Cys Asp Glu Lys Arg Tyr Ile Asn
                325                 330                 335

Ala Leu Ala Pro Leu Leu Lys Glu Gln Gly Phe Ser Asp Ala His Phe
            340                 345                 350

Ile Met Asp Thr Ser Arg Asn Gly Val Gln Pro Thr Lys Gln Gln Ala
            355                 360                 365

Trp Gly Asp Trp Cys Asn Val Ile Gly Thr Gly Phe Gly Val Arg Pro
            370                 375                 380

Thr Thr Asn Thr Gly Asp Ala Leu Gln Asp Ala Phe Val Trp Val Lys
385                 390                 395                 400

Pro Gly Gly Glu Ser Asp Gly Thr Ser Asp Thr Ser Ala Ala Arg Tyr
                405                 410                 415

Asp Ala His Cys Gly Tyr Ser Asp Ala Leu Gln Pro Ala Pro Glu Ala
            420                 425                 430

Gly Thr Trp Phe Gln Ala Tyr Phe Glu Gln Leu Leu Thr Asn Ala Asn
            435                 440                 445

Pro Ser Phe
      450

<210> SEQ ID NO 8
<211> LENGTH: 435
<212> TYPE: PRT
<213> ORGANISM: Aspergillus fumigatus

<400> SEQUENCE: 8

Gln Gln Thr Val Trp Gly Gln Cys Gly Gly Gln Gly Trp Ser Gly Pro
1               5                   10                  15

Thr Ser Cys Val Ala Gly Ala Ala Cys Ser Thr Leu Asn Pro Tyr Tyr
            20                  25                  30

Ala Gln Cys Ile Pro Gly Ala Thr Ala Thr Ser Thr Thr Leu Thr Thr
            35                  40                  45

Thr Thr Ala Ala Thr Thr Thr Ser Gln Thr Thr Thr Lys Pro Thr Thr
        50                  55                  60

Thr Gly Pro Thr Thr Ser Ala Pro Thr Val Thr Ala Ser Gly Asn Pro
65                  70                  75                  80
```

Phe Ser Gly Tyr Gln Leu Tyr Ala Asn Pro Tyr Tyr Ser Ser Glu Val
                85                  90                  95

His Thr Leu Ala Met Pro Ser Leu Pro Ser Ser Leu Gln Pro Lys Ala
            100                 105                 110

Ser Ala Val Ala Glu Val Pro Ser Phe Val Trp Leu Asp Val Ala Ala
        115                 120                 125

Lys Val Pro Thr Met Gly Thr Tyr Leu Ala Asp Ile Gln Ala Lys Asn
130                 135                 140

Lys Ala Gly Ala Asn Pro Ile Ala Gly Ile Phe Val Val Tyr Asp
145                 150                 155                 160

Leu Pro Asp Arg Asp Cys Ala Ala Leu Ala Ser Asn Gly Glu Tyr Ser
                165                 170                 175

Ile Ala Asn Asn Gly Val Ala Asn Tyr Lys Ala Tyr Ile Asp Ala Ile
            180                 185                 190

Arg Ala Gln Leu Val Lys Tyr Ser Asp Val His Thr Ile Leu Val Ile
        195                 200                 205

Glu Pro Asp Ser Leu Ala Asn Leu Val Thr Asn Leu Asn Val Ala Lys
    210                 215                 220

Cys Ala Asn Ala Gln Ser Ala Tyr Leu Glu Cys Val Asp Tyr Ala Leu
225                 230                 235                 240

Lys Gln Leu Asn Leu Pro Asn Val Ala Met Tyr Leu Asp Ala Gly His
                245                 250                 255

Ala Gly Trp Leu Gly Trp Pro Ala Asn Leu Gly Pro Ala Ala Thr Leu
            260                 265                 270

Phe Ala Lys Val Tyr Thr Asp Ala Gly Ser Pro Ala Ala Val Arg Gly
        275                 280                 285

Leu Ala Thr Asn Val Ala Asn Tyr Asn Ala Trp Ser Leu Ser Thr Cys
    290                 295                 300

Pro Ser Tyr Thr Gln Gly Asp Pro Asn Cys Asp Glu Lys Lys Tyr Ile
305                 310                 315                 320

Asn Ala Met Ala Pro Leu Leu Lys Glu Ala Gly Phe Asp Ala His Phe
                325                 330                 335

Ile Met Asp Thr Ser Arg Asn Gly Val Gln Pro Thr Lys Gln Asn Ala
            340                 345                 350

Trp Gly Asp Trp Cys Asn Val Ile Gly Thr Gly Phe Gly Val Arg Pro
        355                 360                 365

Ser Thr Asn Thr Gly Asp Pro Leu Gln Asp Ala Phe Val Trp Ile Lys
    370                 375                 380

Pro Gly Gly Glu Ser Asp Gly Thr Ser Asn Ser Thr Ser Pro Arg Tyr
385                 390                 395                 400

Asp Ala His Cys Gly Tyr Ser Asp Ala Leu Gln Pro Ala Pro Glu Ala
                405                 410                 415

Gly Thr Trp Phe Gln Ala Tyr Phe Glu Gln Leu Leu Thr Asn Ala Asn
            420                 425                 430

Pro Ser Phe
        435

<210> SEQ ID NO 9
<211> LENGTH: 449
<212> TYPE: PRT
<213> ORGANISM: Artificial sequence
<220> FEATURE:
<223> OTHER INFORMATION: Synthetic construct

<400> SEQUENCE: 9

-continued

```
Gln Ala Gln Gln Thr Val Trp Gly Gln Cys Gly Gly Gln Gly Trp Ser
1               5                   10                  15
Gly Pro Thr Ser Cys Val Ala Gly Ser Thr Cys Ser Thr Gln Asn Pro
            20                  25                  30
Tyr Tyr Ala Gln Cys Ile Pro Gly Ser Thr Ala Thr Ser Thr Thr Thr
        35                  40                  45
Thr Ser Thr Thr Thr Thr Thr Thr Thr Ser Thr Thr Thr Thr Thr Thr
    50                  55                  60
Thr Thr Thr Thr Pro Pro Thr Thr Gly Pro Thr Thr Thr Ala Pro Pro
65                  70                  75                  80
Ala Ala Thr Thr Thr Ala Ser Ala Ser Gly Asn Pro Phe Ser Gly Tyr
                85                  90                  95
Gln Leu Tyr Ala Asn Pro Tyr Tyr Ala Ser Glu Val His Ser Leu Ala
            100                 105                 110
Ile Pro Ser Leu Thr Asp Ser Ser Leu Ala Pro Lys Ala Ser Ala Val
            115                 120                 125
Ala Lys Val Pro Ser Phe Val Trp Leu Asp Thr Ala Ala Lys Val Pro
    130                 135                 140
Thr Met Gly Thr Tyr Leu Ala Asp Ile Gln Ala Lys Asn Lys Ala Gly
145                 150                 155                 160
Ala Asn Pro Pro Ile Ala Gly Ile Phe Val Val Tyr Asp Leu Pro Asp
                165                 170                 175
Arg Asp Cys Ala Ala Leu Ala Ser Asn Gly Glu Tyr Ser Ile Ala Asn
            180                 185                 190
Asn Gly Val Ala Asn Tyr Lys Ala Tyr Ile Asp Ser Ile Arg Ala Gln
            195                 200                 205
Leu Val Lys Tyr Ser Asp Val His Thr Ile Leu Val Ile Glu Pro Asp
    210                 215                 220
Ser Leu Ala Asn Leu Val Thr Asn Leu Asn Val Ala Lys Cys Ala Asn
225                 230                 235                 240
Ala Gln Ser Ala Tyr Leu Glu Cys Val Asp Tyr Ala Leu Lys Gln Leu
                245                 250                 255
Asn Leu Pro Asn Val Ala Met Tyr Leu Asp Ala Gly His Ala Gly Trp
            260                 265                 270
Leu Gly Trp Pro Ala Asn Leu Gly Pro Ala Ala Gln Leu Phe Ala Lys
    275                 280                 285
Val Tyr Lys Asn Ala Gly Ser Pro Ala Ala Val Arg Gly Leu Ala Thr
    290                 295                 300
Asn Val Ala Asn Tyr Asn Ala Trp Ser Ile Ser Thr Cys Pro Ser Tyr
305                 310                 315                 320
Thr Gln Gly Asp Pro Asn Cys Asp Glu Lys Arg Tyr Ile Asn Ala Leu
                325                 330                 335
Ala Pro Leu Leu Lys Glu Asn Gly Phe Pro Asp Ala His Phe Ile Met
            340                 345                 350
Asp Thr Ser Arg Asn Gly Val Gln Pro Thr Lys Gln Gln Ala Trp Gly
            355                 360                 365
Asp Trp Cys Asn Val Ile Gly Thr Gly Phe Gly Val Arg Pro Thr Thr
    370                 375                 380
Asn Thr Gly Asp Pro Leu Gln Asp Ala Phe Val Trp Val Lys Pro Gly
385                 390                 395                 400
Gly Glu Ser Asp Gly Thr Ser Asn Thr Ser Ser Pro Arg Tyr Asp Ala
                405                 410                 415
His Cys Gly Tyr Ser Asp Ala Leu Gln Pro Ala Pro Glu Ala Gly Thr
```

```
           420                 425                 430
Trp Phe Gln Ala Tyr Phe Glu Gln Leu Leu Thr Asn Ala Asn Pro Ser
       435                 440                 445
Phe
```

<210> SEQ ID NO 10
<211> LENGTH: 48
<212> TYPE: DNA
<213> ORGANISM: Artificial sequence
<220> FEATURE:
<223> OTHER INFORMATION: Synthetic construct

<400> SEQUENCE: 10
cagaagtgtg ctaatgctca gagtgcttac gaggagtgca tcaactat                    48

<210> SEQ ID NO 11
<211> LENGTH: 30
<212> TYPE: DNA
<213> ORGANISM: Artificial sequence
<220> FEATURE:
<223> OTHER INFORMATION: Synthetic construct

<400> SEQUENCE: 11
gtaagcactc tgagcattag cacacttctg                                        30

<210> SEQ ID NO 12
<211> LENGTH: 48
<212> TYPE: DNA
<213> ORGANISM: Artificial sequence
<220> FEATURE:
<223> OTHER INFORMATION: Synthetic construct

<400> SEQUENCE: 12
cttagcccgg ccgctcaact ctttgcttcc gcctaccaga atgcaagc                    48

<210> SEQ ID NO 13
<211> LENGTH: 30
<212> TYPE: DNA
<213> ORGANISM: Artificial sequence
<220> FEATURE:
<223> OTHER INFORMATION: Synthetic construct

<400> SEQUENCE: 13
ggaagcaaag agttgagcgg ccgggctaag                                        30

<210> SEQ ID NO 14
<211> LENGTH: 48
<212> TYPE: DNA
<213> ORGANISM: Artificial sequence
<220> FEATURE:
<223> OTHER INFORMATION: Synthetic construct

<400> SEQUENCE: 14
ctggctccat tgcttcagca acagggatgg gagtcagttc actttatc                    48

<210> SEQ ID NO 15
<211> LENGTH: 30
<212> TYPE: DNA
<213> ORGANISM: Artificial sequence
<220> FEATURE:
<223> OTHER INFORMATION: Synthetic construct

<400> SEQUENCE: 15
ccatccctgt tgctgaagca atggagccag                                        30

<210> SEQ ID NO 16
<211> LENGTH: 48
<212> TYPE: DNA
<213> ORGANISM: Artificial sequence
<220> FEATURE:
<223> OTHER INFORMATION: Synthetic construct

<400> SEQUENCE: 16
cagaagtgtg ctaatgctca gagtgcttac aaggagtgca tcaactat                48

<210> SEQ ID NO 17
<211> LENGTH: 30
<212> TYPE: DNA
<213> ORGANISM: Artificial sequence
<220> FEATURE:
<223> OTHER INFORMATION: Synthetic construct

<400> SEQUENCE: 17
gtaagcactc tgagcattag cacacttctg                                    30

<210> SEQ ID NO 18
<211> LENGTH: 48
<212> TYPE: DNA
<213> ORGANISM: Artificial sequence
<220> FEATURE:
<223> OTHER INFORMATION: Synthetic construct

<400> SEQUENCE: 18
cttagcccgg ccgctcaact ctttgcttcc gcgtaccaga atgcaagc                48

<210> SEQ ID NO 19
<211> LENGTH: 30
<212> TYPE: DNA
<213> ORGANISM: Artificial sequence
<220> FEATURE:
<223> OTHER INFORMATION: Synthetic construct

<400> SEQUENCE: 19
ggaagcaaag agttgagcgg ccgggctaag                                    30

<210> SEQ ID NO 20
<211> LENGTH: 48
<212> TYPE: DNA
<213> ORGANISM: Artificial sequence
<220> FEATURE:
<223> OTHER INFORMATION: Synthetic construct

<400> SEQUENCE: 20
cagaagtgtg ctaatgctca gagtgcttac gtggagtgca tcaactat                48

<210> SEQ ID NO 21
<211> LENGTH: 30
<212> TYPE: DNA
<213> ORGANISM: Artificial sequence
<220> FEATURE:
<223> OTHER INFORMATION: Synthetic construct

<400> SEQUENCE: 21
gtaagcactc tgagcattag cacacttctg                                    30

<210> SEQ ID NO 22
<211> LENGTH: 40
<212> TYPE: DNA
<213> ORGANISM: Artificial sequence
<220> FEATURE:
<223> OTHER INFORMATION: Synthetic construct

```
<400> SEQUENCE: 22
ttgcagccaa gatctctgca cagcaaacca tgtggggtca                              40

<210> SEQ ID NO 23
<211> LENGTH: 40
<212> TYPE: DNA
<213> ORGANISM: Artificial sequence
<220> FEATURE:
<223> OTHER INFORMATION: Synthetic construct

<400> SEQUENCE: 23
taaatcatat taattaagct ttagaaagag gggttggcgt                              40

<210> SEQ ID NO 24
<211> LENGTH: 30
<212> TYPE: DNA
<213> ORGANISM: Artificial sequence
<220> FEATURE:
<223> OTHER INFORMATION: Synthetic construct

<400> SEQUENCE: 24 gctattttc taacaaagca tcttagatta                                          30

<210> SEQ ID NO 25
<211> LENGTH: 30
<212> TYPE: DNA
<213> ORGANISM: Artificial sequence
<220> FEATURE:
<223> OTHER INFORMATION: Synthetic construct

<400> SEQUENCE: 25
gctgatcccc tcgttttcgg aaacgctttg                                         30

<210> SEQ ID NO 26
<211> LENGTH: 30
<212> TYPE: DNA
<213> ORGANISM: Artificial sequence
<220> FEATURE:
<223> OTHER INFORMATION: Synthetic construct

<400> SEQUENCE: 26
ggtccgttaa ggttagaaga aggctacttt                                         30

<210> SEQ ID NO 27
<211> LENGTH: 30
<212> TYPE: DNA
<213> ORGANISM: Artificial sequence
<220> FEATURE:
<223> OTHER INFORMATION: Synthetic construct

<400> SEQUENCE: 27
cctattccga agttcctatt ctctagaaag                                         30

<210> SEQ ID NO 28
<211> LENGTH: 30
<212> TYPE: DNA
<213> ORGANISM: Artificial sequence
<220> FEATURE:
<223> OTHER INFORMATION: Synthetic construct

<400> SEQUENCE: 28
ttgctatgta catcgatgct ggtcatgctg                                         30

<210> SEQ ID NO 29
```

```
<211> LENGTH: 30
<212> TYPE: DNA
<213> ORGANISM: Artificial sequence
<220> FEATURE:
<223> OTHER INFORMATION: Synthetic construct

<400> SEQUENCE: 29
cagcatgacc agcatcgatg tacatagcaa                                          30

<210> SEQ ID NO 30
<211> LENGTH: 30
<212> TYPE: DNA
<213> ORGANISM: Artificial sequence
<220> FEATURE:
<223> OTHER INFORMATION: Synthetic construct

<400> SEQUENCE: 30
gagcagaaat acatcaacgc tctggctcca                                          30

<210> SEQ ID NO 31
<211> LENGTH: 30
<212> TYPE: DNA
<213> ORGANISM: Artificial sequence
<220> FEATURE:
<223> OTHER INFORMATION: Synthetic construct

<400> SEQUENCE: 31
tggagccaga gcgttgatgt atttctgctc                                          30

<210> SEQ ID NO 32
<211> LENGTH: 500
<212> TYPE: DNA
<213> ORGANISM: Talaromyces leycettanus

<400> SEQUENCE: 32
tgtaagatca ccctctgtgt attgcaccat gcggtctctc ctggctcttg cccctaccct         60
gctcgcgcct gttgttcagg ctcagcaaac catgtggggt caatgcggtg gtcaggctg         120
gaccggacct accatctgtg tagcaggcgc gacatgcagc acacagaacc cttggtatgc        180
gcagtgcacc ccagcaccta ccgcgccgac gaccttgcaa acaacaacta cgacgagctc        240
gaaatcgtcc acgaccacga gctcgaagtc gtccacgacc acaggtggaa gtggcggtgg        300
aactacgacc tcaacgtcag ccaccatcac cgcggctcca tctggtaacc catactccgg        360
ataccagctc tatgtgaacc aggaatactc gtccgaggtg tacgcgtctg ctattccttc        420
ccttaccggc actctggtcg cgaaggcaag cgccgcggca gaggtgccat ctttcctgtg        480
gctggacact gcctccaagg                                                    500

<210> SEQ ID NO 33
<211> LENGTH: 500
<212> TYPE: DNA
<213> ORGANISM: Talaromyces leycettanus

<400> SEQUENCE: 33
gaggtgccat ctttcctgtg gctggacact gcctccaagg tgccactgat gggcacttac         60
ttgcaggata tccaggcgaa gaacgctgct ggcgccaacc caccatatgc cggtcaattc        120
gtggtttacg acttgccgga tcgtgattgc gctgcattgg ccagcaatgg agagtactcc        180
attgctaaca atggtgttgc caactacaag gcttacatcg actccatccg cgcgcttctt        240
gttcaatact cgaacgtcca tgtcatcctt gtgatcgagc cgacagcttt ggccaacctt        300
gtcaccaacc tgaatgttca gaagtgtgct aatgctcaga gtgcttacct ggagtgcatc        360
```

```
aactatgccc tcactcagtt gaacctcaag aacgttgcta tgtacatcga tgctggtcat    420
gctggatggc tcggctggcc cgccaacctt agcccggccg ctcaactctt tgcttccgta    480
taccagaatg caagctcccc                                                500
```

<210> SEQ ID NO 34
<211> LENGTH: 500
<212> TYPE: DNA
<213> ORGANISM: Talaromyces leycettanus

<400> SEQUENCE: 34

```
tgcttccgta taccagaatg caagctcccc agctgccgtt cgcggcctgg caaccaacgt     60
ggccaactat aatgcctggt cgatcgccac ttgcccatct tacacccaag gcgaccccaa    120
ctgcgacgag cagaaataca tcaacgctct ggctccattg cttcagcaac agggatggtc    180
atcagttcac tttatcaccg ataccggccg taacggtgtc cagcctacca agcagaatgc    240
ctggggtgac tggtgcaacg ttatcggaac cggcttcggt gtccgtccca ccaccaacac    300
tggcgatcca ttggaggatg ctttcgtctg ggtcaagcct ggtggtgaga gtgatggtac    360
ttccaactcc acttcgcctc gctacgacgc ccactcgcgt tacagtgatg ctcttcagcc    420
tgctcctgag gctggtacct ggttcgaggc ttactttgag caactcctta ccaacgccaa    480
cccctctttc taatagttaa                                                500
```

<210> SEQ ID NO 35
<211> LENGTH: 48
<212> TYPE: DNA
<213> ORGANISM: Artificial sequence
<220> FEATURE:
<223> OTHER INFORMATION: Synthetic constuct

<400> SEQUENCE: 35

```
gcagctcacc tgaagaggct tgtaagatca ccctctgtgt attgcacc                  48
```

<210> SEQ ID NO 36
<211> LENGTH: 49
<212> TYPE: DNA
<213> ORGANISM: Artificial sequence
<220> FEATURE:
<223> OTHER INFORMATION: Synthetic construct

<400> SEQUENCE: 36

```
ccaacgccaa cccctctttc taatagttaa ttaaggcttt cgtgaccgg                 49
```

<210> SEQ ID NO 37
<211> LENGTH: 57
<212> TYPE: DNA
<213> ORGANISM: Saccharomyces cerevisiae

<400> SEQUENCE: 37

```
atgcttttgc aagccttcct tttccttttg gctggttttg cagccaagat ctctgca       57
```